United States Patent
So et al.

(10) Patent No.: US 11,565,258 B2
(45) Date of Patent: Jan. 31, 2023

(54) METHOD AND APPARATUS FOR THE ANALYSIS AND IDENTIFICATION OF MOLECULES

(71) Applicant: Genvida Technology Company Limited, Hong Kong (CN)

(72) Inventors: Daniel Wai-Cheong So, Palo Alto, CA (US); Chi Yip Ho, Toronto (CA)

(73) Assignee: GENVIDA TECHNOLOGY COMPANY LIMITED, Hong Kong (CN)

( * ) Notice: Subject to any disclaimer, the term of this patent is extended or adjusted under 35 U.S.C. 154(b) by 718 days.

(21) Appl. No.: 16/338,996

(22) PCT Filed: Oct. 2, 2017

(86) PCT No.: PCT/US2017/054753
§ 371 (c)(1),
(2) Date: Apr. 3, 2019

(87) PCT Pub. No.: WO2018/067457
PCT Pub. Date: Apr. 12, 2018

(65) Prior Publication Data
US 2020/0038868 A1 Feb. 6, 2020

Related U.S. Application Data

(60) Provisional application No. 62/403,690, filed on Oct. 3, 2016.

(51) Int. Cl.
*G01N 33/487* (2006.01)
*B01L 3/00* (2006.01)
*C12Q 1/6869* (2018.01)

(52) U.S. Cl.
CPC ............. *B01L 3/502761* (2013.01); *B01L 3/502715* (2013.01); *C12Q 1/6869* (2013.01);
(Continued)

(58) Field of Classification Search
None
See application file for complete search history.

(56) References Cited

U.S. PATENT DOCUMENTS

| 5,795,782 A | 8/1998 | Church et al. |
| 6,015,714 A | 1/2000 | Baldarelli et al. |

(Continued)

FOREIGN PATENT DOCUMENTS

| CN | 1606137 A | 4/2005 |
| CN | 101225436 A | 7/2008 |

(Continued)

OTHER PUBLICATIONS

Bai et al, Nanoscale, vol. 6, pp. 8900-8906, published 2014.*

(Continued)

*Primary Examiner* — Robert T. Crow
(74) *Attorney, Agent, or Firm* — Law Offices of Albert Wai-Kit Chan, PLLC

(57) ABSTRACT

An apparatus and method for performing analysis and identification of molecules have been presented. In one embodiment, a portable molecule analyzer includes a sample input/output connection to receive a sample, a nanopore-based sequencing chip to perform analysis on the sample substantially in real-time, and an output interface to output result of the analysis.

19 Claims, 26 Drawing Sheets

(52) U.S. Cl.
CPC ............... *G01N 33/48721* (2013.01); *B01L 2200/0663* (2013.01); *B01L 2300/0645* (2013.01); *B01L 2300/0848* (2013.01); *B01L 2300/0896* (2013.01)

(56) References Cited

U.S. PATENT DOCUMENTS

| | | |
|---|---|---|
| 6,267,872 B1 | 7/2001 | Akeson et al. |
| 6,362,002 B1 | 3/2002 | Denison et al. |
| 6,413,792 B1 | 7/2002 | Sauer et al. |
| 6,464,842 B1 | 10/2002 | Golovchenko et al. |
| 6,465,193 B2 | 10/2002 | Akeson et al. |
| 6,482,639 B2 | 11/2002 | Snow et al. |
| 6,616,895 B2 | 9/2003 | Dugas et al. |
| 6,627,067 B1 | 9/2003 | Branton et al. |
| 6,673,615 B2 | 1/2004 | Denison et al. |
| 6,746,594 B2 | 6/2004 | Akeson et al. |
| 6,783,643 B2 | 8/2004 | Golovchenko et al. |
| 6,806,534 B2 | 10/2004 | Dokumaci et al. |
| 6,806,543 B2 | 10/2004 | Yamakawa et al. |
| 6,846,702 B1 | 1/2005 | Barth |
| 6,905,878 B2 | 6/2005 | Ghadiri et al. |
| 6,936,433 B2 | 8/2005 | Akeson et al. |
| 7,001,792 B2 | 2/2006 | Sauer et al. |
| 7,060,507 B2 | 6/2006 | Akeson et al. |
| 7,189,503 B2 | 3/2007 | Akeson et al. |
| 7,238,485 B2 | 7/2007 | Akeson et al. |
| 7,258,838 B2 | 8/2007 | Li et al. |
| 7,347,921 B2 | 3/2008 | Barth et al. |
| 7,361,313 B2 | 4/2008 | Chan et al. |
| 7,410,564 B2 | 8/2008 | Flory |
| 7,435,353 B2 | 10/2008 | Golovchenko et al. |
| 7,468,271 B2 | 12/2008 | Golovchenko et al. |
| 7,504,505 B2 | 3/2009 | Shenoy et al. |
| 7,582,490 B2 | 9/2009 | Golovchenko et al. |
| 7,625,706 B2 | 12/2009 | Akeson et al. |
| 7,678,562 B2 | 3/2010 | Ling |
| 7,741,130 B2 | 6/2010 | Lee et al. |
| 7,883,839 B2 | 2/2011 | Donnelly et al. |
| 8,926,904 B2 * | 1/2015 | So ............... B82Y 30/00 422/82.02 |
| 2003/0003609 A1 | 1/2003 | Sauer et al. |
| 2003/0040173 A1 | 2/2003 | Fonash et al. |
| 2003/0136679 A1 | 7/2003 | Bohn et al. |
| 2004/0051154 A1 | 3/2004 | Yamakawa et al. |
| 2004/0144658 A1 | 7/2004 | Flory |
| 2005/0014162 A1 | 1/2005 | Barth et al. |
| 2005/0127035 A1 | 6/2005 | Ling |
| 2005/0202444 A1 | 9/2005 | Zhu |
| 2005/0227239 A1 * | 10/2005 | Joyce ............... C12Q 1/6816 435/287.2 |
| 2006/0063171 A1 | 3/2006 | Akeson et al. |
| 2006/0063196 A1 | 3/2006 | Akeson et al. |
| 2006/0231419 A1 | 10/2006 | Barth et al. |
| 2006/0275911 A1 | 12/2006 | Wang et al. |
| 2007/0048745 A1 | 3/2007 | Joyce et al. |
| 2007/0065832 A1 | 3/2007 | Stenger et al. |
| 2007/0131646 A1 | 6/2007 | Donnelly et al. |
| 2007/0178507 A1 | 8/2007 | Wu et al. |
| 2007/0281329 A1 | 12/2007 | Akeson et al. |
| 2007/0298511 A1 | 12/2007 | Kang et al. |
| 2008/0032290 A1 | 2/2008 | Young |
| 2008/0102504 A1 | 5/2008 | Akeson et al. |
| 2008/0187915 A1 | 8/2008 | Polonsky et al. |
| 2008/0248561 A1 | 10/2008 | Golovchenko et al. |
| 2008/0257859 A1 | 10/2008 | Golovchenko et al. |
| 2008/0280776 A1 | 11/2008 | Bashir et al. |
| 2009/0029477 A1 | 1/2009 | Meller et al. |
| 2009/0084688 A1 | 4/2009 | Leburton et al. |
| 2009/0130386 A1 | 5/2009 | Golovchenko et al. |
| 2009/0136682 A1 | 5/2009 | Branton et al. |
| 2009/0136958 A1 | 5/2009 | Gershow et al. |
| 2009/0298072 A1 | 12/2009 | Ju |
| 2010/0025249 A1 | 2/2010 | Polonsky et al. |
| 2010/0292101 A1 * | 11/2010 | So ............... B32B 37/18 506/16 |
| 2010/0331194 A1 * | 12/2010 | Turner ............... G01N 27/44791 506/2 |
| 2014/0231274 A1 * | 8/2014 | Oki ............... G01N 33/48721 205/792 |
| 2015/0069329 A1 | 3/2015 | Jeon et al. |

FOREIGN PATENT DOCUMENTS

| | | |
|---|---|---|
| CN | 102498201 A | 6/2012 |
| JP | 4719906 B2 | 7/2011 |
| JP | 2012-110258 A | 6/2012 |
| KR | 10-2012-0024691 A | 3/2012 |
| WO | 2005017025 A2 | 2/2005 |
| WO | 2008042018 A2 | 4/2008 |
| WO | 2010132603 A1 | 11/2010 |

OTHER PUBLICATIONS

Branton, D. et al. "The Potential and Challenges of Nanopore Sequencing", Nature Biotechnology, Oct. 2008, pp. 1146-1153, vol. 26, No. 10.

Clarke, J. et al., "Continuous Base Identification for Single-Molecule Nanopore DNA Sequencing," Nature Nanotechnology, 2009, pp. 1-6.

Clarke, J. et al., Supplementary Information, Nature Nanotechnology, 2009, 17 pages.

De Blois, R.W. et al., "Electrokinetic Measurements with Submicron Particles and Pores by the Resistive Pulse Technique," Journal of Colloid and Interface Science, The Academic Press, Inc., Sep. 1977, pp. 323-335, vol. 61, No. 2.

De Blois, R.W. et al., "Counting and Sizing of Submicron Particles by the Resistive Pulse Technique," The Review of Scientific Instruments, Jul. 1970, pp. 909-916, vol. 41, No. 7.

Eid, J. et al., "Real-Time DNA Sequencing from Single Polymerase Molecules," Science, Jan. 2, 2009, pp. 133-138, vol. 323.

Kasianowicz, J.J. et al., "Characterization of Individual Polynucleotide Molecules Using a Membrane Channel," Proceedings of the National Academy of Sciences of the United States of America, Nov. 26, 1996, p. 13770-13773, vol. 93, No. 24.

Xu, L. et al., "Nanopantography: A New Method for Massively Parallel Nanopatterning Over Large Areas," Nano Letters, 2005, pp. 2563-2568, vol. 5, No. 12.

Loughran, Michael, "IBM Research Aims to Build Nanoscale DNA Sequencer to Help Drive Down Cost of Personalized Genetic Analysis", accessed at: http://www-03.ibm.com/press/US/en/pressrelease/28558.wss on Feb. 11, 2010, published Oct. 6, 2009, 3 pages.

Chiou, Chi-Han, et al., "Minimal dead-volume connectors for microfluidics using PDMS casting techniques", Journal of Micromechanics and Microengineering, vol. 14, Aug. 9, 2004, pp. 1484-1490.

Zhang, Chunsun, et al., "Micropumps, microvalves, and micromixers within PCR microfluldic chips: Advances and trends", Biotechnology Advances, vol. 25, 2007, pp. 483-514.

Gracheva, Maria E., et al., "Simulation of the electric response of DNA translocation through a semiconductor nanopore-capacitor", Nanotechnology, vol. 17, Jan. 6, 2006, pp. 622-633.

Cui et al., Nanogap Electrodes towards Solid State Single-Molecule Transistors, Small, 2015, 11, No. 46, p. 6115-6141.

Ventra et ai., Decoding DNA, RNA and peptides with quantum tunnelling, Nature Nanotechnology, vol. 11, Feb. 2016, p. 117-126.

Li et al., Nanogap Electrodes, Advanced Materials, 2010, 22, p. 286-30.

Storm, A.J. et al., "Fabrication of Solid-State Nanopores with Single-Nanometre Precision," Nature Materials, Nature Publishing Group, Jul. 13, 2003, pp. 537-540, vol. 2, No. 8.

* cited by examiner

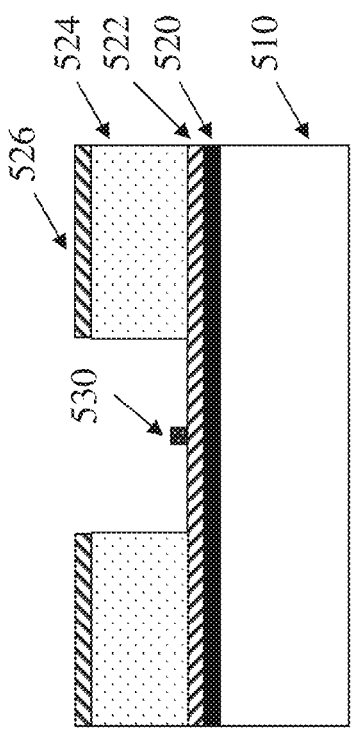
FIG. 5C
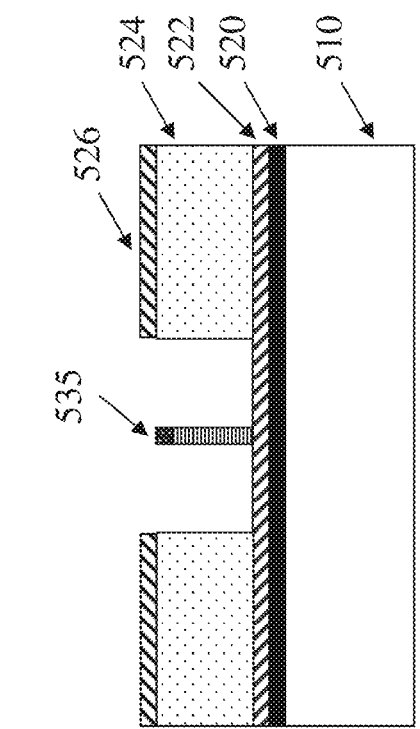
FIG. 5D
FIG. 5A
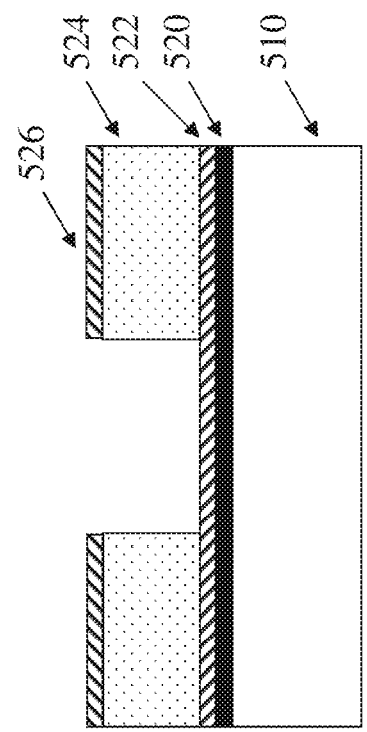
FIG. 5B

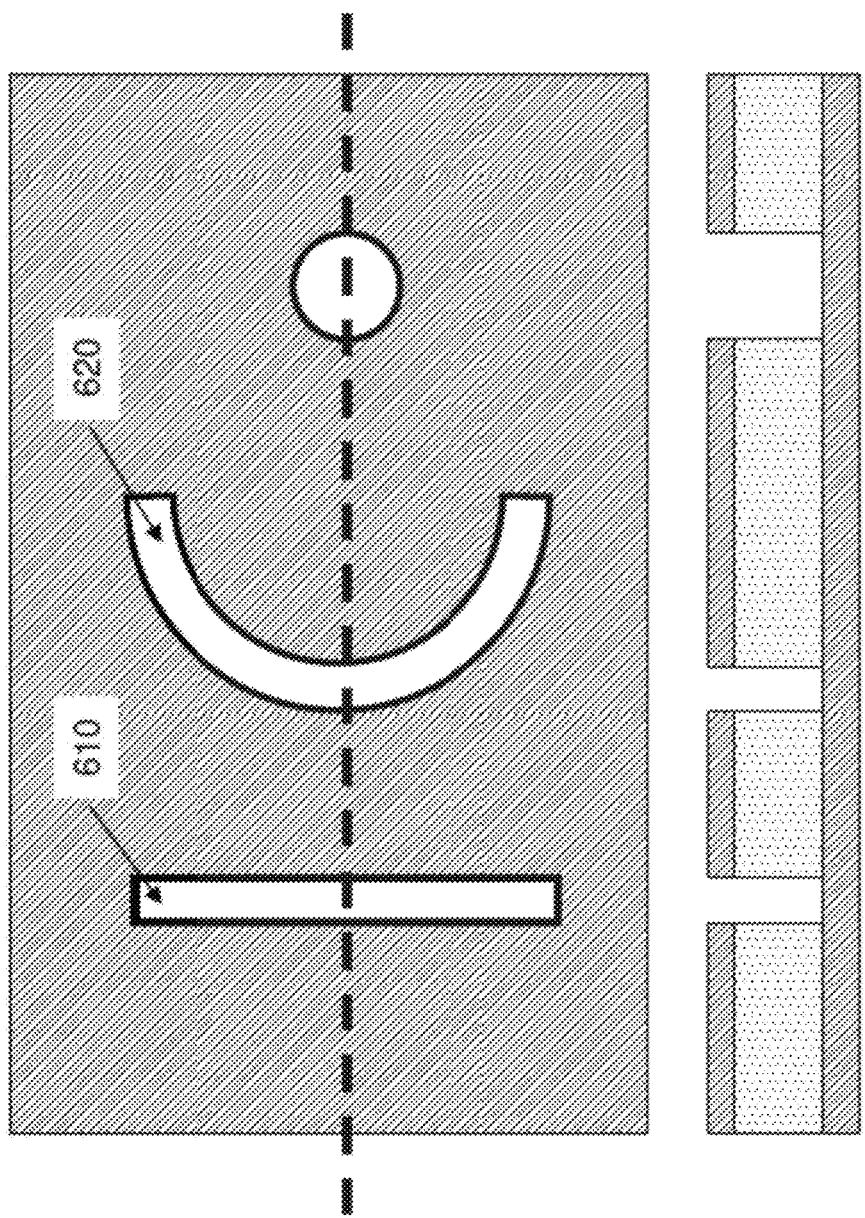

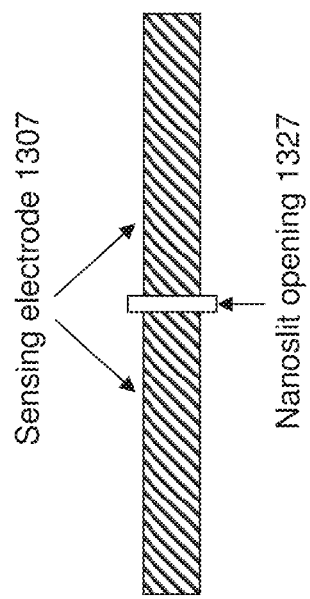

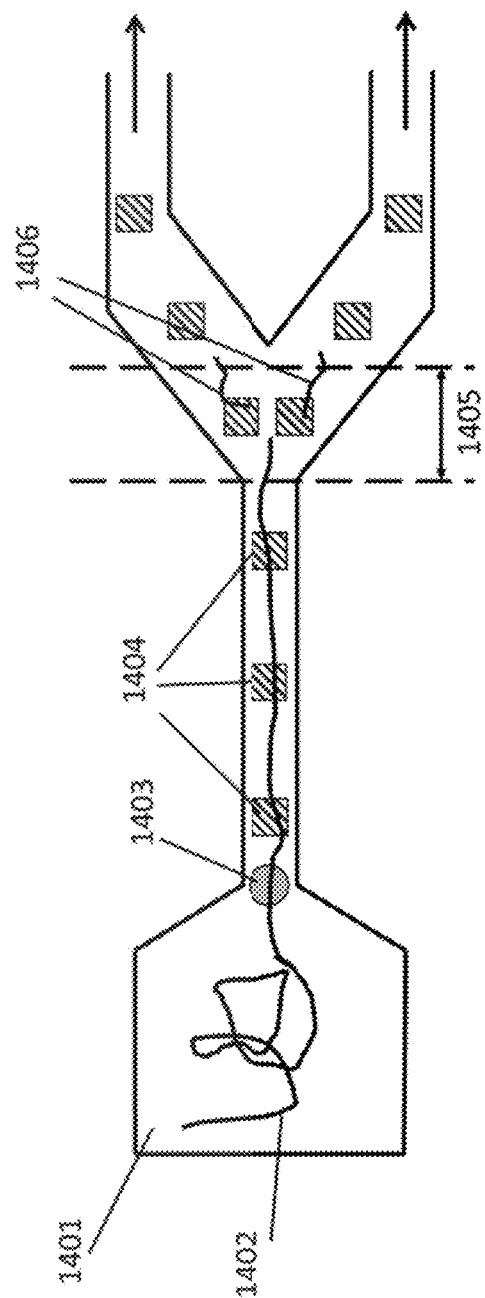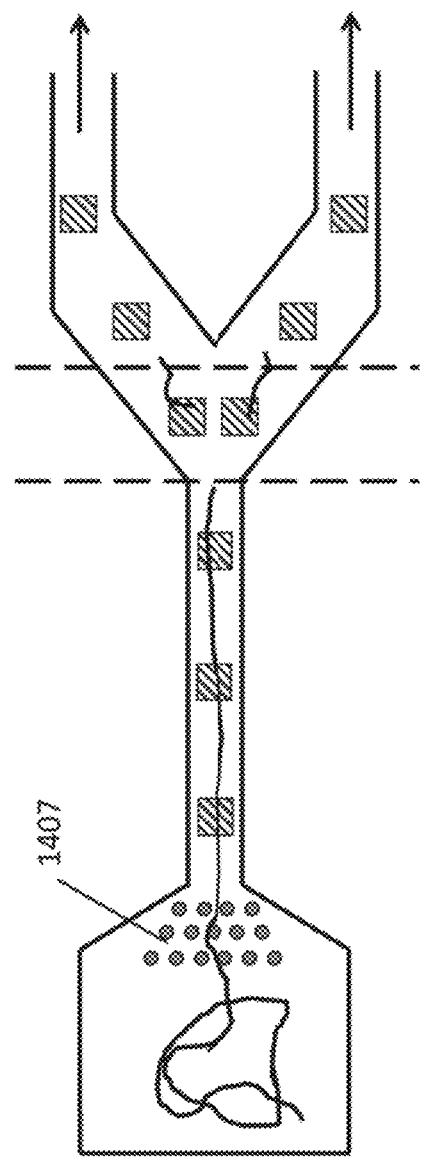
FIG. 14A
FIG. 14B

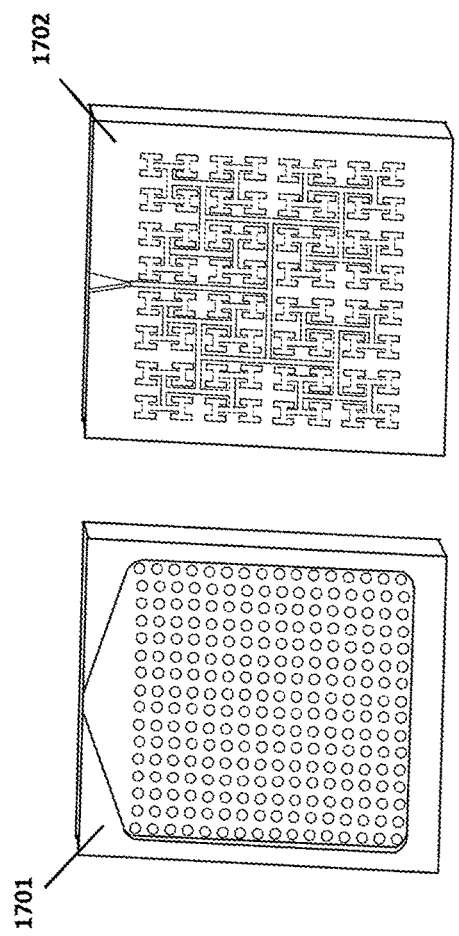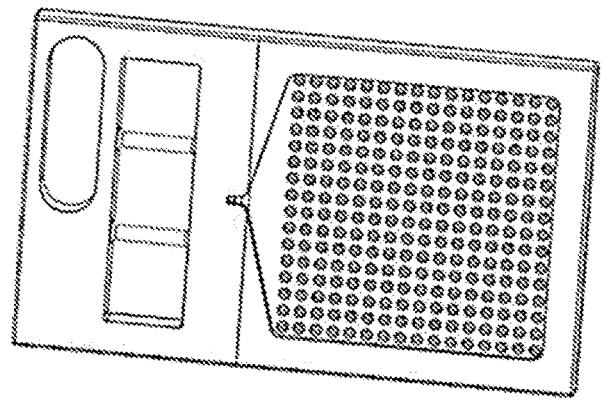
FIG.17
FIG.18

METHOD AND APPARATUS FOR THE ANALYSIS AND IDENTIFICATION OF MOLECULES

TECHNICAL FIELD

The present invention relates generally to analyze and identify of molecules, and in particular to providing a real-time, portable, nanopore-based molecule analysis apparatus.

BACKGROUND

Nucleic acids, deoxyribonucleic acid (DNA), and/or ribose nucleic acid (RNA) are present and have unique sequences in every living organism. It lends itself naturally as a definitive identification for various bio-agents. Therefore, analysis of nucleic acids, DNA, and/or RNA, which is broadly referred to as genomic analysis herein, is very useful in studying living organisms. However, the currently commercially available nucleic acid sequencing technologies, such as microarray, pyrosequencing, sequencing by synthesis and sequencing by ligation are very limited in various aspects. For instance, some or all of these technologies cannot perform real-time analysis, require lengthy sample nucleic acid amplification procedures and protocols (such as polymerase chain reaction), have long turnaround time (typically takes about several days to weeks to analyze a small fragment of the sample nucleic acid), have high operation cost (some of which use expensive chemical reagents), have high false-positive error rates, and are non-portable.

Because of the above limitations of the current nucleic acid sequencing technologies, people working in the fields, such as medical professionals, security personnel, scientists, etc., cannot perform genomic analysis on-site locally. Rather, field workers have to collect and transport samples to specialized laboratories to be analyzed for days, or even weeks, in order to identify the nucleic acids present in the sample. Such lengthy tedious process can hardly meet today's need for genomic analysis, especially during epidemic outbreaks, such as the foot-and-mouth epidemic in United Kingdom, the Severe Acute Respiratory Syndrome (SARS) outbreak in Asia, and the recent H1N1 flu (also commonly known as swine flu) outbreak in Mexico and the United States. Using the current nucleic acid sequencing technologies, it is difficult, if not impossible, for the authorities to formulate a swift and informed decision, which could have an enormous safety and economic impact on the society.

To address the shortfalls of the above nucleic acid sequencing technologies, scientists have developed various nanopore-based sequencing technologies. Recently, Professor Hagan Bayley of Oxford University and his co-workers demonstrated long read with 99.8% accuracy using the α-haemolysin in a bio-nanopore experiment. Based on the established detection speed, an array of 256×256 nanopores is generally sufficient to analyze the human genome in its entirety within about thirty minutes. This would be a watershed triumph if one can successfully realize the bio-nanopore array. However, one drawback for bio-nanopores is the relative short lifetime, typically several hours to days, of the proteins and enzymes used in forming the bio-nanopores.

Solid state nanopore is a more robust alternative to bio-nanopore since there is no bio-reagent involved in the construction of the solid state nanopores. However, conventional lithography technologies employed in semiconductor industry are not capable of defining the 2-nm feature size required by the solid-state nanopore-based sequencing technologies. Thus far, different fabrication techniques, for instance, electron/ion milling, have been used to sequentially carve the nanopores one at a time. But these techniques cannot be scaled to produce the 256×256 array with affordable cost and reasonable production time.

BRIEF DESCRIPTION OF THE DRAWINGS

The present invention is illustrated by way of example, and not of limitation, in the figures of the accompanying drawings in which:

FIGS. 5A-5I illustrate one embodiment of a additive method for fabricating a nanopore and/or a nanopore array;

FIG. 6A illustrates one embodiment of a nanoring and one embodiment of a nanoslit;

FIG. 13C illustrates a top view of one embodiment of sensing electrodes and nanoslit in planar electrode implementation;

1402 to a dissociation zone 1405 where heating causes the dsDNA to dissociate into short strands of ssDNA. 1406 before being transported downstream by guiding electrodes.

Figure 14C:
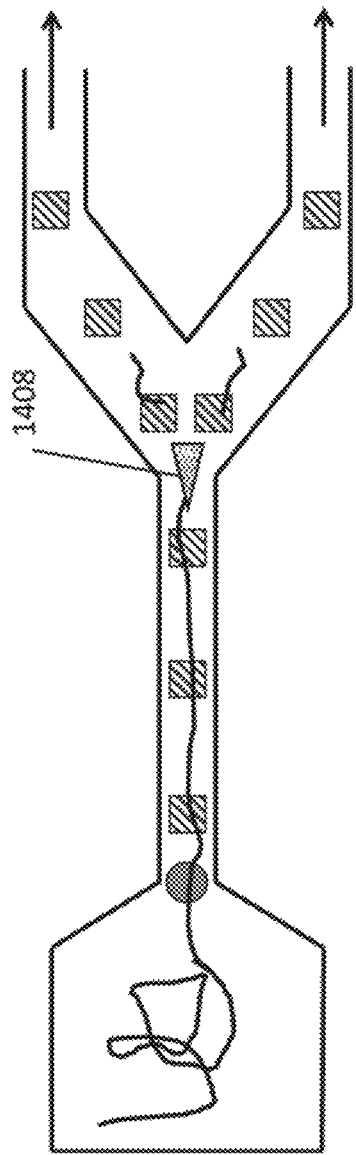
FIG. 14A shows an embodiment for straightening the nicked dsDNA. A DNA pump 1403, defined as a DNA-translocating protein that can be anchored to a fixed location and act as a DNA processing motor in an oriented manner, e.g. FtsK family of proteins, is used for actively transport one end of the nicked dsDNA 1402 into a channel with guiding electrodes 1404 which then transport nicked dsDNA
Figure 14D:
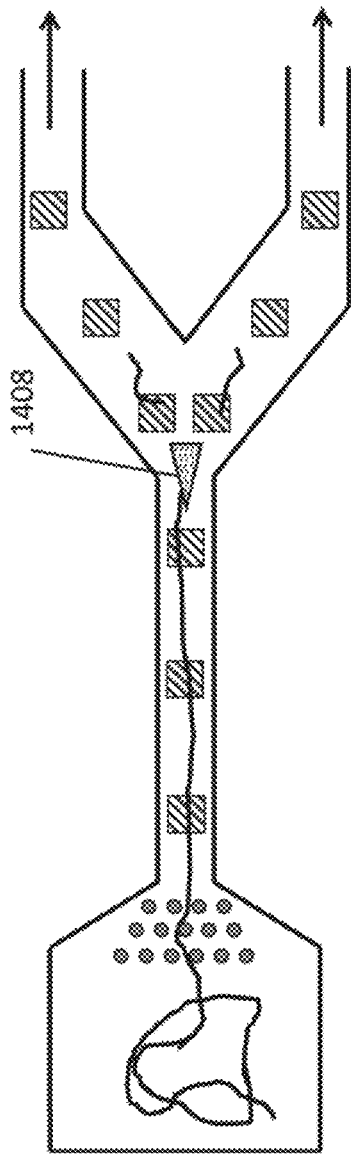
Figure 14E:
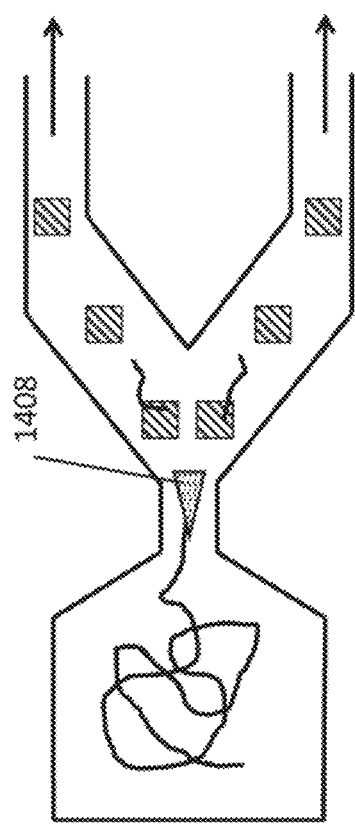

FIG. 14 B shows an embodiment where the DNA pump in FIG. 14 A is replaced by an array of micro/nano-pillars 1407.

FIG. 14 C shows the same embodiment as FIG. 14 A except that helicase 1408 instead of heat is used in the dissociation zone.

FIG. 14 D shows the same embodiment as FIG. 14 B except that helicase 1408 instead of heat is used in the dissociation zone.

FIG. 14 E shows an embodiment where the nicked dsDNA is directly fed to the dissociation zone without straightening the dsDNA.

Figure 15:
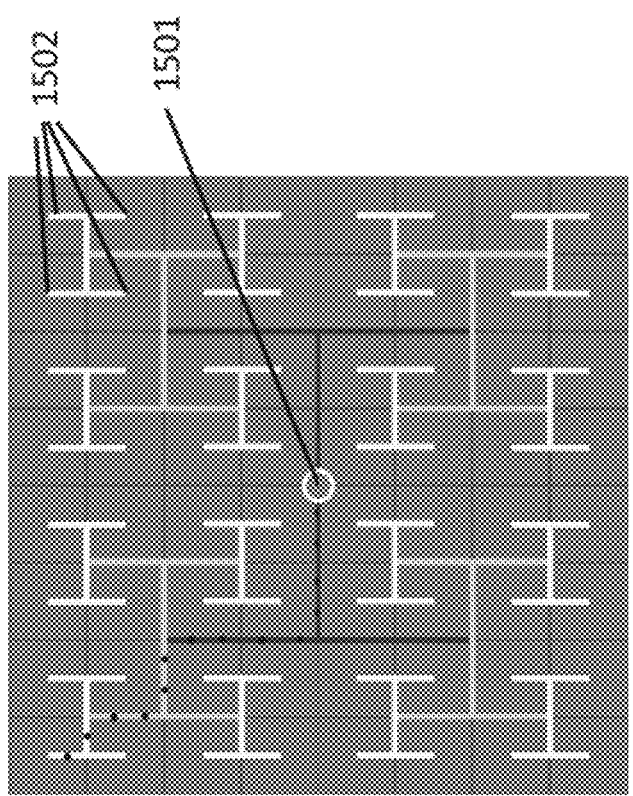

FIG. 15 shows a set of channels with H-tree structure where there is a single inlet 1501 and multiple outlets 1502. The H-tree structure ensures that the path length from the inlet 1501 to any of the outlets 1502 is the same.

Figure 16:
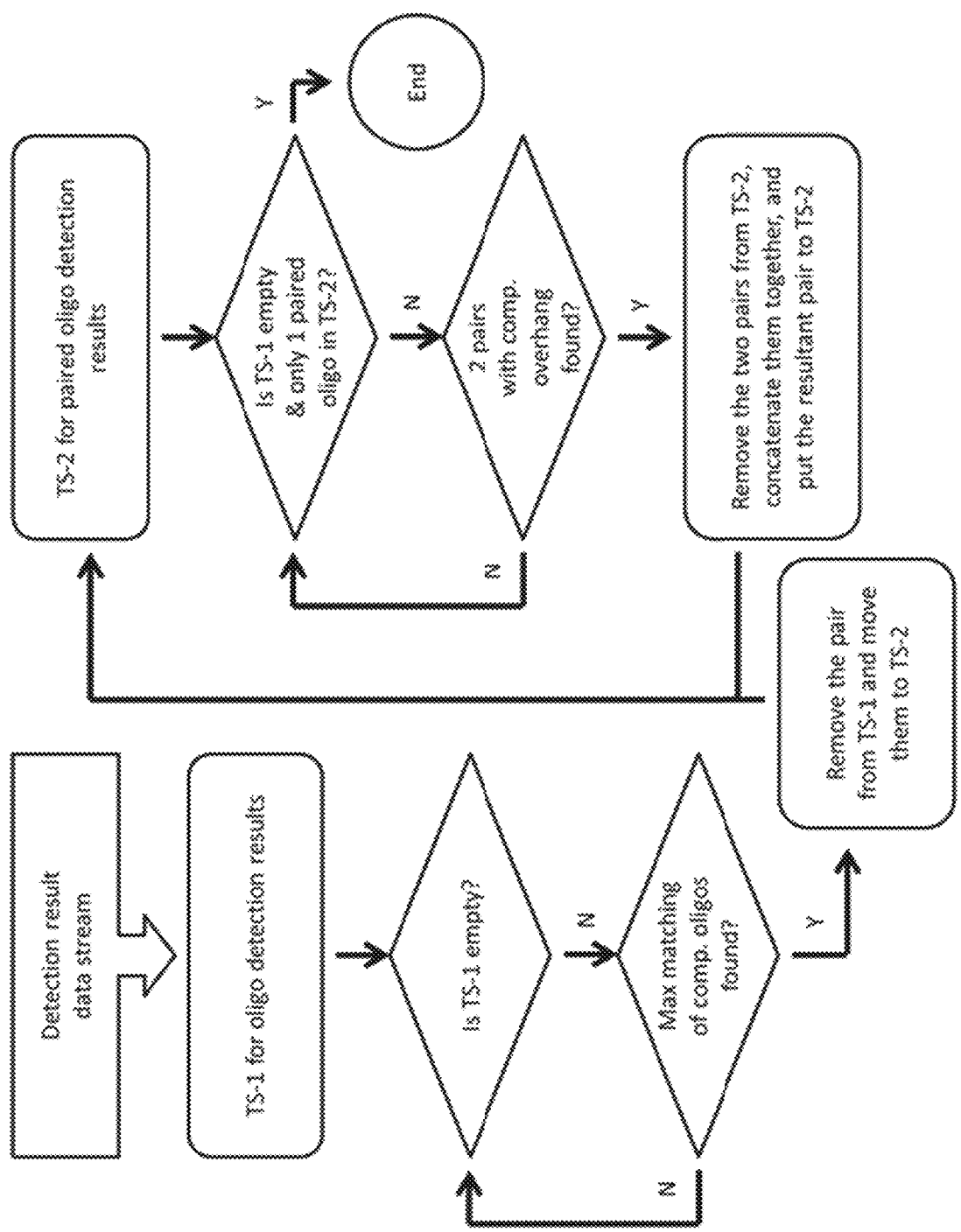

FIG. 16 shows a flow chart for the concatenation algorithm. Since the order of availability of the oligonucleotide sequencing results follows closely with the order of the dissociation of the oligonucleotides from the nicked dsDNA, the temporary storages, TS-1 and TS-2, can be implemented with relatively simple data structure, such as queue, stack, linked list or hash table.

FIG. 17 shows an example of the well array and the H-tree network in the real-time dPCR biochip.

FIG. 18 shows an example of the complete real-time dPCR module.

Figure 19:
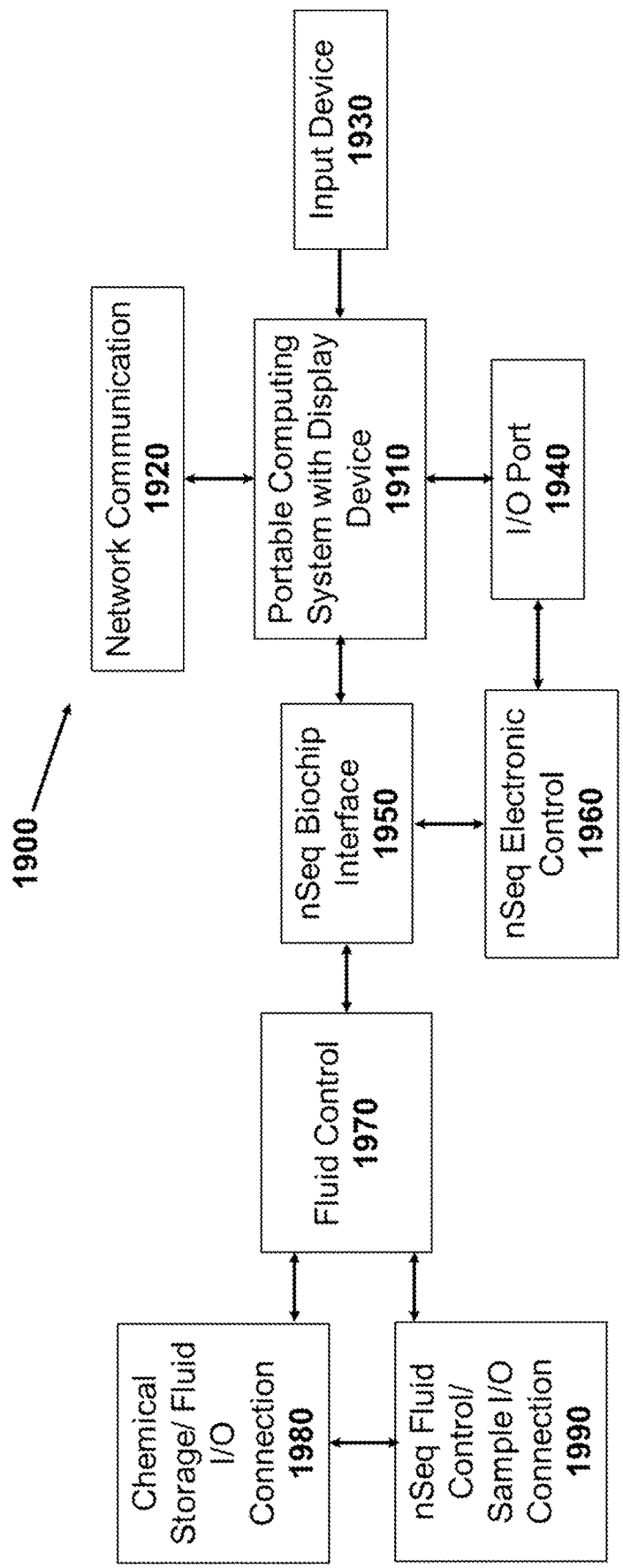
Figure 20:
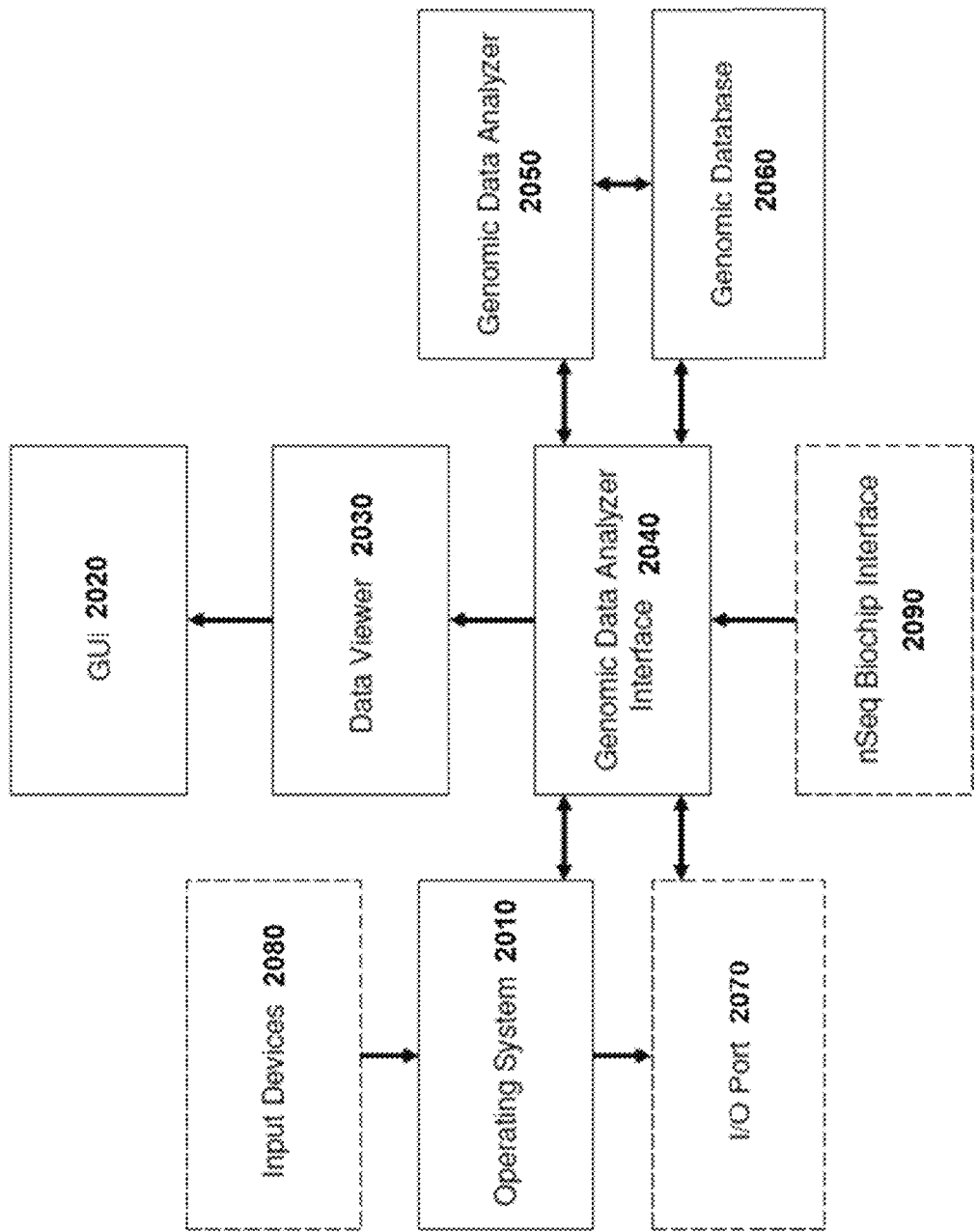

FIG. 19 illustrates a high-level hardware architecture of one embodiment of a nanopore-based sequencer; and FIG. 20 illustrates a high-level architecture of the software and related hardware components for the operating system and the genomic analysis software in one embodiment of a nanopore-based sequencer.

DETAILED DESCRIPTION

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention.

Figure 1:
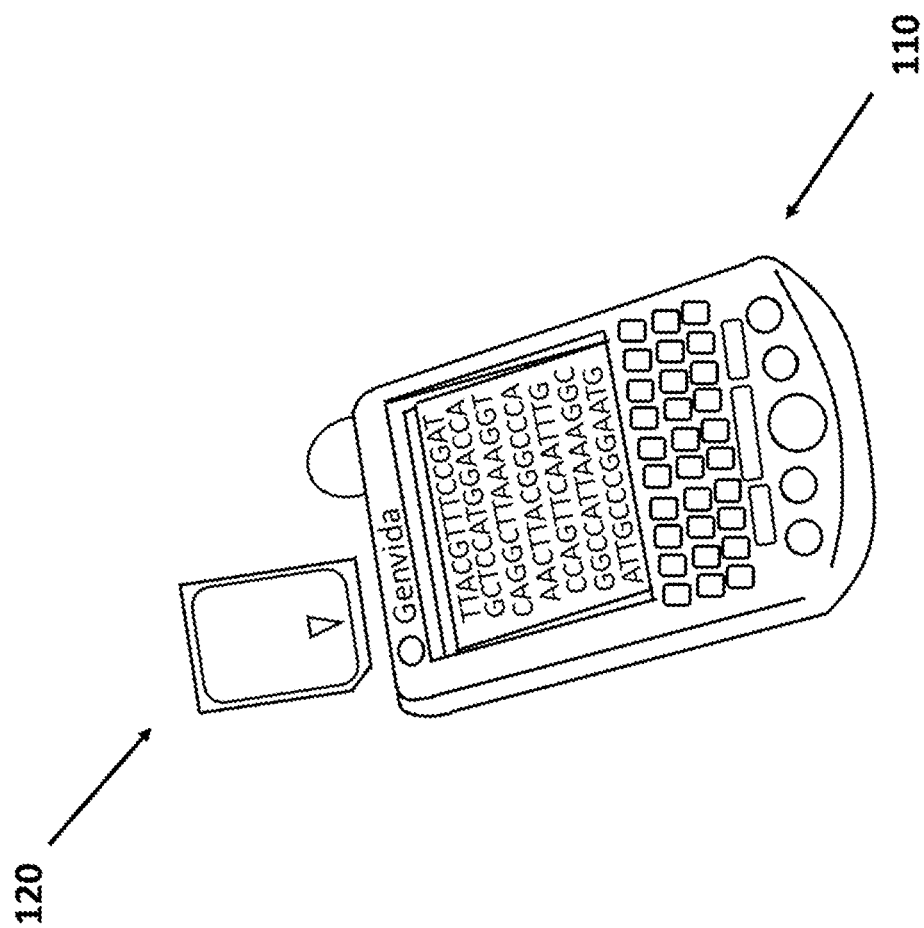
FIG. 1 illustrates one embodiment of a nanopore-based sequencer and an associated nanopore-based sequencing biochip.
Figure 2B:
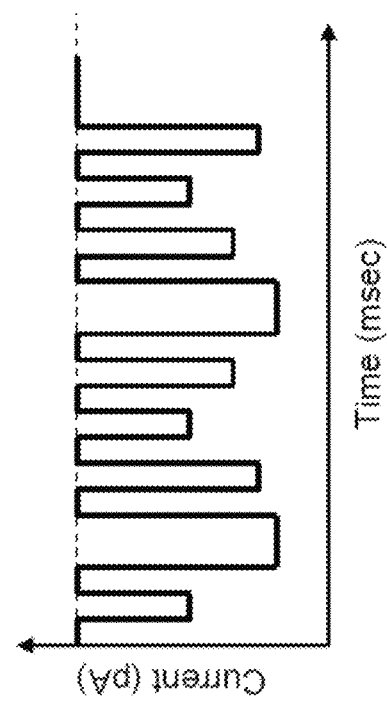
FIG. 2B illustrates a corresponding exemplary electrical readout of the nucleic acid sequence as compared with the background signal of an empty pore.
Figure 2A:
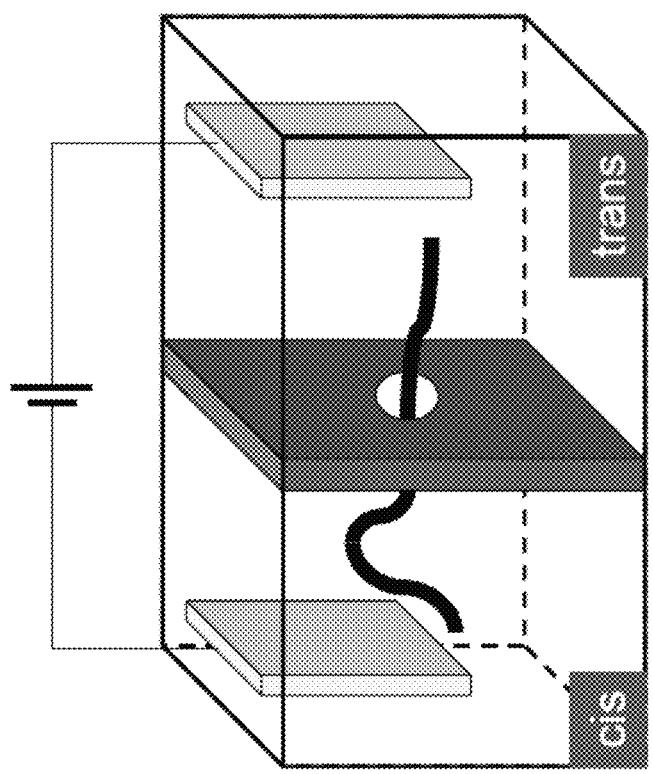
FIG. 2A illustrates one embodiment of a translocation process of a molecule during the detection and analysis of nanopore based nucleic acid sequencing.

Various embodiments of an apparatus and a method to perform analysis and identification of molecules, such as, nucleic acids, amino acids, peptides, proteins and polymers, and nanometer sized particles, such as carbon nanotubes, silicon nanorods and coated/uncoated gold nanoparticles, are described below. Note that the following discussion is focus on one example of molecule analysis, namely genomic analysis, in order to illustrate the concept. One of skilled in the art would readily recognize that the technique disclosed herein is applicable to analyze and identify molecules in general. In one embodiment, a nanopore-based sequencer is a portable genomic analysis system. FIG. 1 illustrates one embodiment of a portable nanopore-based sequencer 110 and an associated nanopore-based sequencing biochip 120. During detection and analysis, a molecule in a sample under test is electrophoretically driven in solution through a nanoscale pore (also referred to as a nanopore), as illustrated in FIG. 2A. In some embodiments, the size of the nanopore is about 2 nm. Note that the size of the nanopores may vary in different embodiments. For example, the nanopores are of fixed identical size in some embodiments. In some alternate embodiments, the nanopores are of different sizes. Furthermore, the shape of the nanopores may also vary in the same embodiment, or in different embodiments, such as circles, ovals, elongated slits, etc. Contingent upon the relative size and travelling speed of the molecule in the space confined within the nanopore, various electrical characteristics, such as current pulses of different amplitudes and durations, as represented in FIG. 2B, can be observed and utilized to identify the molecule. As a result, direct read of the nucleic acid sequence can be achieved without destroying the molecule under test. In other words, measurements can be made on the nucleic acid sequence while keeping the nucleic acid sequence intact. In one embodiment, the electrical readout is the turn-on voltage and/or conductance/current of the molecules. In another embodiment, the molecules could be nucleotides from a strand of DNA. Theoretical values for each of the corresponding nucleosides have been obtained by Kletsov et al. [Ref. Kletsov et al., "Ab initio electron propagator calculations of transverse conduction through DNA nucleotide bases in 1-nm nanopore corroborate third generation sequencing", Biochimica et Biophysica Acta, Volume 1860, Issue 1, Part A, January 2016, Pages 140-145]

Multiple fabrication techniques may be utilized to massively produce the nanopore array, which includes an array of about 2-nm pores in some embodiments, without fundamental limitations. Details of some exemplary fabrication techniques are discussed in details below to illustrate the concept. One of skill in the art would appreciate that other comparable fabrication techniques or variations to these techniques may be adopted to produce the nanopore array. By incorporating into a network of micro-/nano-fluidic channels, the nanopore-based sequencer can accurately decipher the genome with unprecedented speed and without human intervention.

Besides the small form-factor and speed in genomic analysis, some embodiments of the nanopore-based sequencer offer the following additional advantages. One of the advantages is ready production of future proof to any mutations in the bio-agents. This is possible because nanopore-based sequencing is a direct read technique whose results do not require prior knowledge of the genome under test. Furthermore, some embodiments of the nanopore-based sequencer are operable in extreme conditions and unclean environment because sterility and cleanliness are always ensured for the nanopores as the nanopores are always enclosed inside the nanopore-based sequencing biochip and are not exposed to any unwanted foreign substances during the entire analysis process.

As a handheld portable device, some embodiments of the nanopore-based sequencer can accelerate the advancement in many different industries and science. For instance, in commerce as well as research and development, some embodiments of the nanopore-based sequencer may be useful in basic research, pharmacogenomics, bacterial diagnostics, pathogen detection, agriculture, food industries, biofuel, etc. As further examples, some embodiments of the nanopore-based sequencer may be useful in rapid DNA forensics, port-of-entry bio-screening, etc.

Nanopore Array for Nanopore-Based Sequencing

In the 1970s, based on the resistive-pulse technique of the Coulter Counter, DeBlois and colleagues successfully demonstrated the use of single submicron diameter pores in characterizing particles by their sizes and electrophoretic mobility. Subsequently, Deamer proposed the idea of using nanometer sized pores for gene sequencing. He and his colleagues demonstrated that single-strand DNA (ssDNA) and RNA molecules can be driven through a pore-forming protein and detected by their effect on the ionic current through this nanopore. Given the recently demonstrated high sequencing speed, the progress of nanopore-based sequencing is largely hampered by the lack of an inexpensive and parallel-write fabrication process to create a large array of nanopores for rapid genomic analysis. Many of the conventional lithography methods, electron milling, ion milling, and silicon etch back are not viable means to manufacture the nanopore array required for real-time genomic analysis. Until recently, Donnelly and colleagues in the University of Houston developed some embodiments of nanopantography that can massively produce 2-nm nanopore arrays without much limitation. According to their simulation results, nanopantography is capable of defining holes or dots with size as small as 1-nm. By incorporating the technologies of micro-/nano-fluidics, nanopantography opens up the possibility of achieving real-time or near real-time genomic analysis systems.

Figure 3:
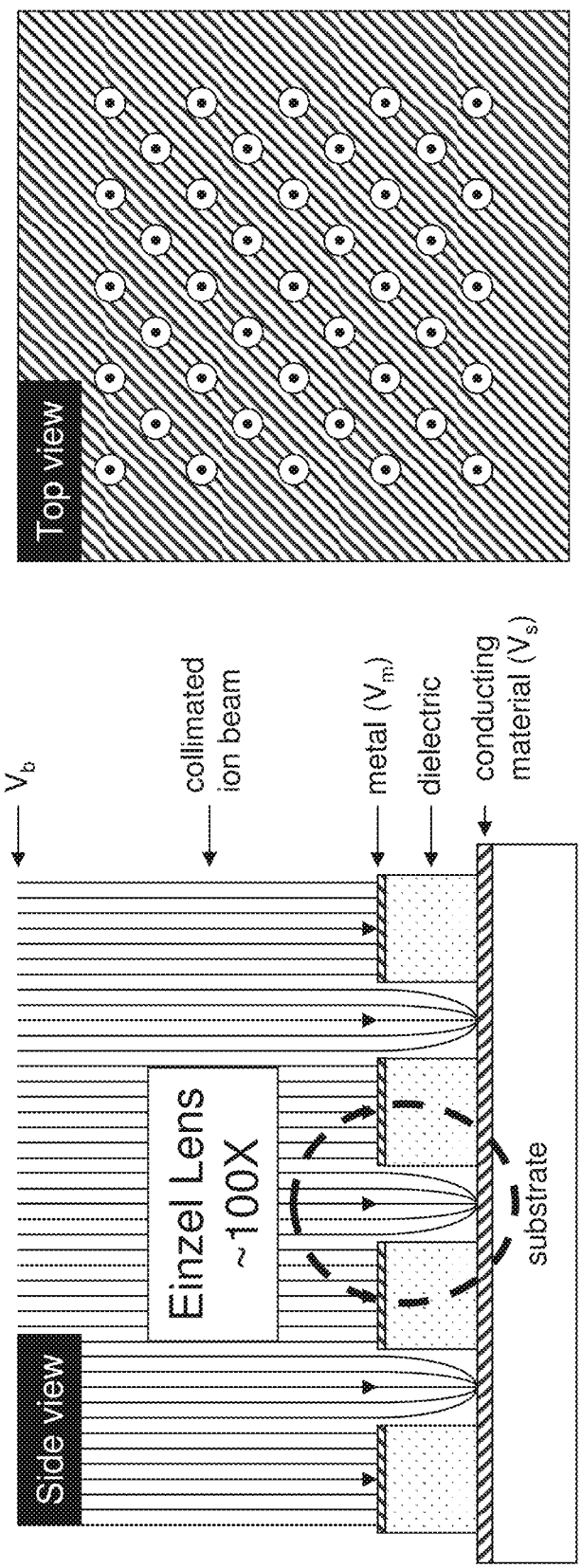
FIG. 3 illustrates a side view and a top view of one embodiment of an Einzel lens used in the nanopantography for both etch and deposition.

In nanopantography, a broad, collimated, monoenergetic ion beam is directed at an array of submicron-diameter electrostatic lenses (also referred to as Einzel lenses, as shown in FIG. 3) fabricated on the conductive substrate, e.g., doped silicon (Si) wafer. By applying appropriate voltages to the lens electrodes, the "beamlets" entering the lenses are focused to spots that can be 100 times smaller than the diameters of the lenses. This means a 1-nm feature can be defined by a 100-nm lens, which can be handled by the photolithographic techniques used in present semiconductor processing. Also, each lens writes its own nanometer feature on the substrate, therefore, nanopantography is a parallel-write process, very different from the sequential writing of the focused electron beam or ion beam. Because the lens array is part of the substrate, the method is substantially immune to misalignment caused by vibrations or thermal expansion. The size of the nanometer features is controlled by the size of the pre-defined lenses, whose diameters could be identical or different, i.e., an array of identical or different nanometer features can be processed substantially simultaneously. With an Ar+ beam in the presence of $Cl_2$ gas, 10-nm diameter, 100-nm deep etched Si holes have been demonstrated. Etching may occur only in the holes for which a voltage is applied to the top metal layer so that the ion beamlets are focused. The rest of the holes will have no voltage applied to the top metal layer, the beamlets will not be focused, and the current density will be too small to cause any appreciable etching.

With the nanopantography, there are two methods, namely the subtractive method and the additive method, to fabricate the nanopores for genomic analysis. One embodiment of a direct etch method is first discussed below, and then followed by discussion of one embodiment of an indirect etch method.

Figure 4C:
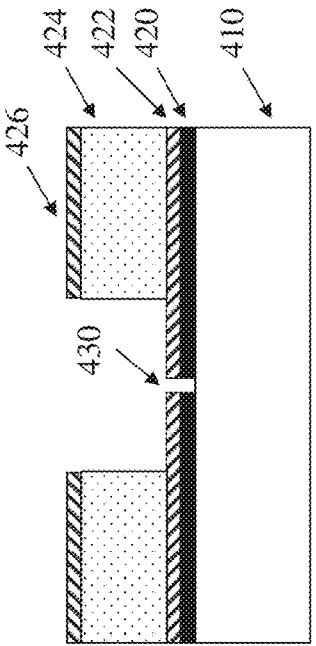
FIGS. 4A-4E illustrate one embodiment of an subtractive method for fabricating a nanopore and/or a nanopore array.

A. One Embodiment of a Subtractive Method for Fabricating Nanopores and/or Nanopore Array FIGS. 4A-4E illustrate one embodiment of a subtractive method for fabricating a nanopore and/or a nanopore array. Referring to FIG. 4A, nitride 420 is deposited on a Si (100) wafer 410. In FIG. 4B, the bottom conducting material 422, doped silicon or metal, is deposited, followed by the dielectric spacer 424, and the top metal layer 426. Then a number of Einzel lenses are defined. Referring to FIG. 4C, the nanopantographic etch is performed on the conducting material 422 to define the nanometer holes 430, which are used as hardmask for the nanopore etch in the nitride layer 420.

Figure 4D:
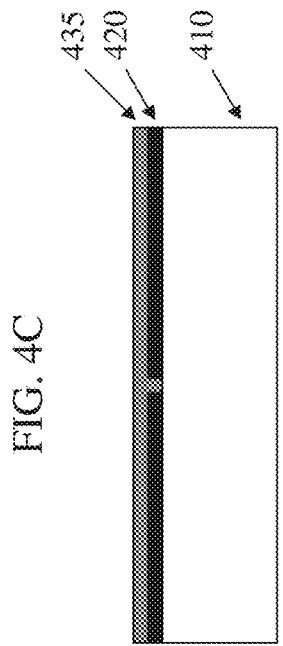
Figure 4E:
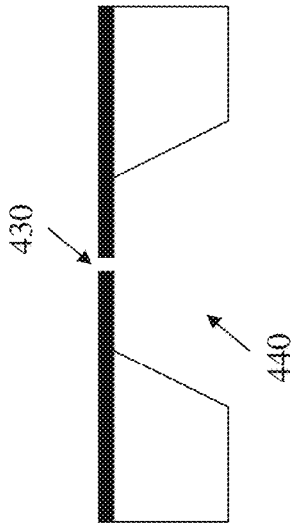
Figure 4A:
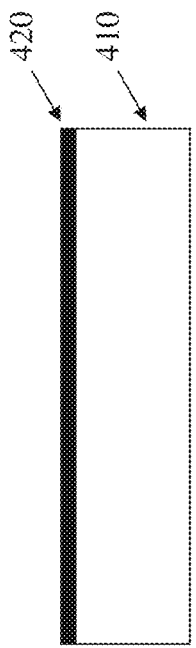
Figure 4B:
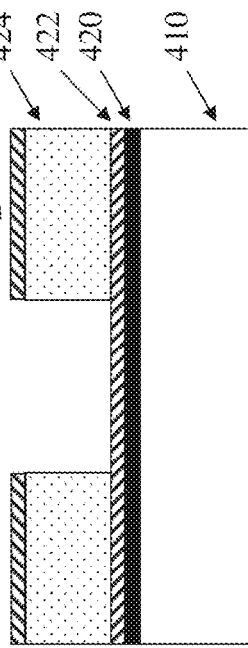

In FIG. 4D, the Einzel lenses are removed. Then the nanopores 430 are coated with oxide 435 for protection. Finally, in FIG. 4E, the bottom cavity 440 of the measurement chamber is formed by chemical mechanical polishing (CMP), lithographic technique and potassium hydroxide (KOH) etch on the backside of the silicon substrate 410. The oxide layer 435 is then removed to reveal the nanopores 430.

Figure 5G:
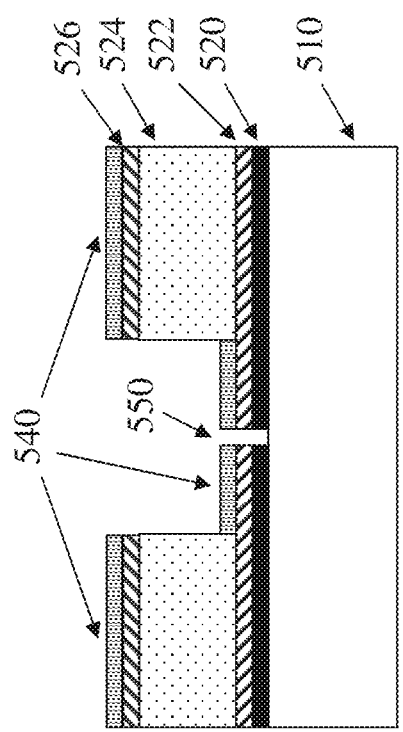
Figure 5E:
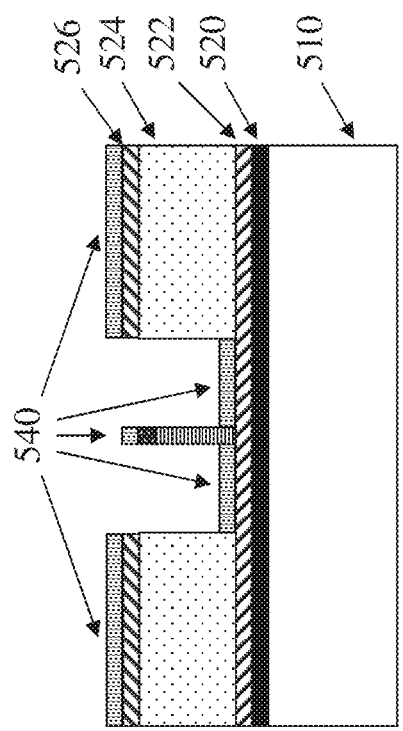
Figure 5F:
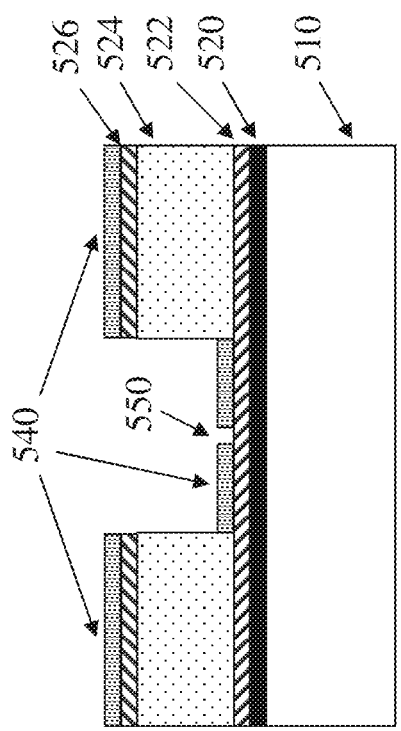
Figure 5H:
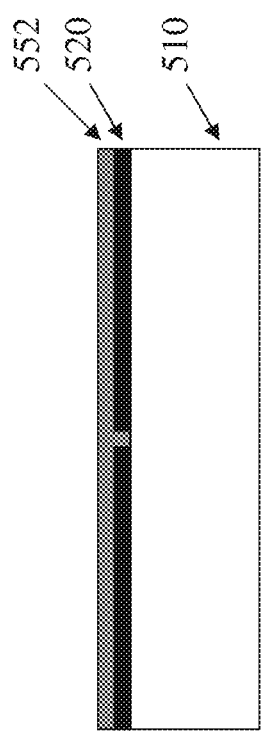
Figure 5I:
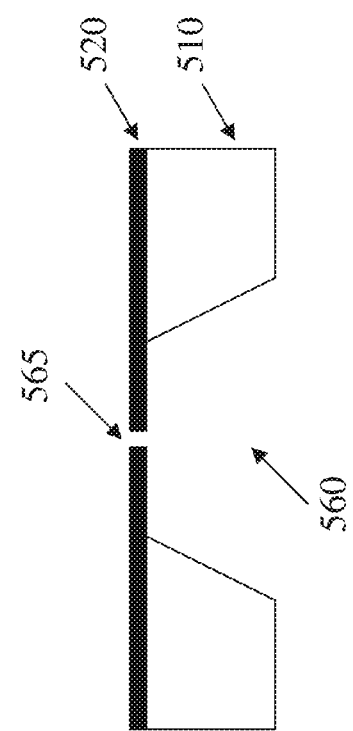

B. One Embodiment of a Additive Method for Fabricating Nanopore and/or Nanopore Array FIGS. 5A-5I illustrate one embodiment of an additive method for fabricating a nanopore and/or a nanopore array. Referring to FIG. 5A, nitride 520 is deposited on a Si (100) water 510. In FIG. 5B, the bottom conducting material 522, doped silicon or metal, the dielectric spacer 524, and the top metal layer 526 are deposited. Then the Einzel lenses are defined. In FIG. 5C, the nano-seed 530 for nanorod or nanotube growth is deposited. In FIG. 5D, the nanorod or nanotube 535 is grown. In FIG. 5E, oxide 540 is deposited. In FIG. 5F, the nanorod or nanotube 535 is removed. The remaining oxide nanometer hole 550 is used as hardmask for the conductive layer and the nitride layer. In FIG. 5G, a pattern is transferred from the oxide layer 540 to conductive layer 522, then to nitride layer 520. In FIG. 5H, the Einzel lenses are removed, followed by removal of the oxide layer 540. The nanopores are coated with oxide 552 for protection. Finally, in FIG. 5I, the bottom cavity 560 of the measurement chamber is formed by CMP, lithographic technique and KOH etch on the backside of the silicon substrate 510. The oxide layer 552 is then removed to reveal the nanopores 565.

Figure 6B:
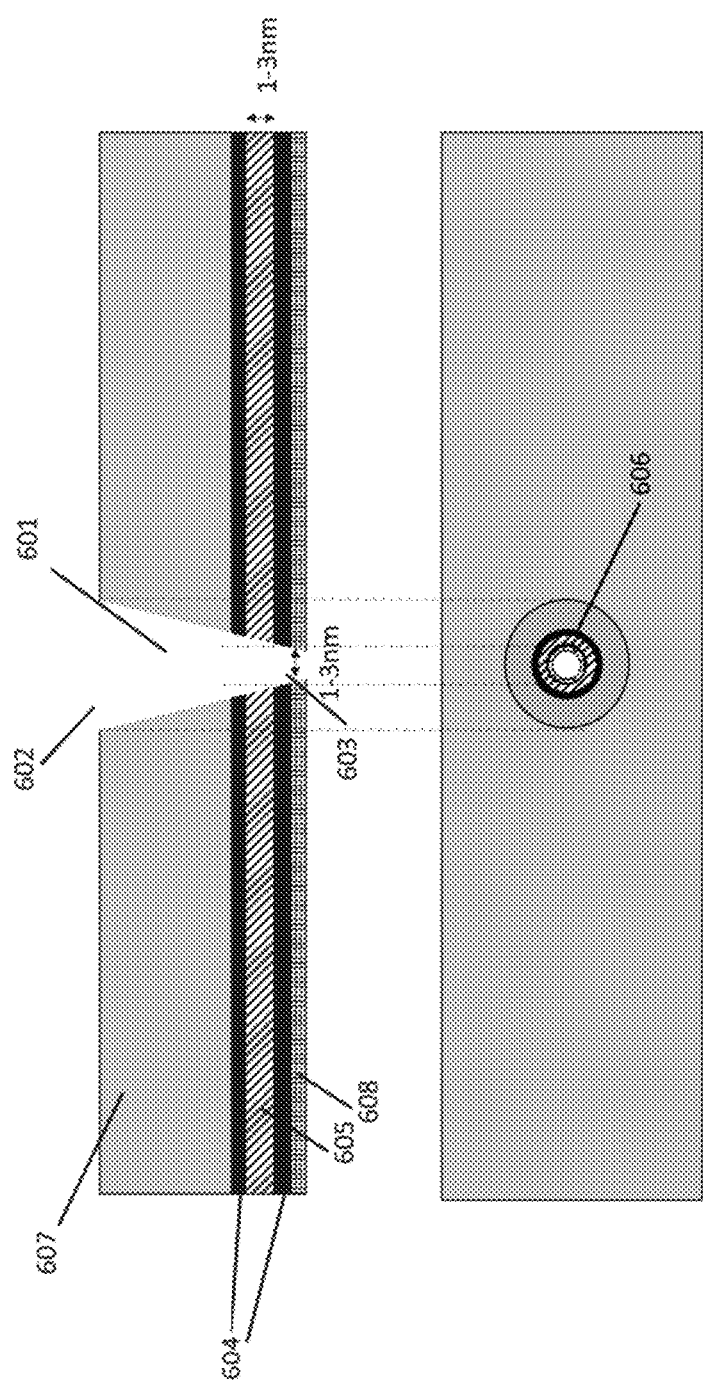
FIG. 6B illustrates an embodiment of the funnel shaped nanopores on a thin film located on a wafer.

FIG. 6A illustrates one embodiment of a nanoslit and one embodiment of a nanoring usable in some embodiments of the invention. The elongated nano-sized nanoslits 610 and nanorings 620 can be defined by some embodiments of the subtractive method with Einzel lenses which is discussed above) with openings in the shape of a rectangle and a semi-circle, respectively, as depicted in FIG. 6A. Based on the disclosure made herein, it should be apparent to one of skilled in the art that any two-dimensional shapes can be defined using similar patterning technique. Since the wafer stage is substantially stationary during the entire process in some embodiments, this non-circular patterning method solves at least three of the major technical issues confronted by the conventional method of tilting the wafer stage. First, there is no need for precise control of the tilting angle and speed of the wafer stage. Second, it generally overcomes the line-broadening effect and the line-width non-uniformity introduced by tilting the wafer relative to the incoming beam of ions. Third, it allows different shapes and sizes of patterns to be defined at about the same time. In one embodiment, nanopantography produces an array of funnel-shaped nanopores on a thin film located on a wafer. FIG. 6B shows an example of the funnel shaped nanopores on a thin film located on a wafer. Each of the funnel-shaped nanopores 601 has a large opening 602 at one surface and a small opening at the other surface 603. In one embodiment, the larger opening 602 facilitates receiving of molecules while the smaller opening 603 is for confining a single molecule within a space for measurement of the identification parameters. The small opening 603 has a dimension comparable to the size of the molecule. In one embodiment, the small opening has a diameter of 1, 2 or 3 nm. In one embodiment, the thin film is a composite thin film comprising multiple layers. The thin film may consist of at least three layers comprising two conductive layers 604 sandwiching a dielectric layer 605. The two conductive layers 604 can be carbon based materials, such as graphene, or metal, such as iridium.

In one embodiment, the conductive layers 604 can be further processed to function as electrodes for detecting identity of molecules. The dielectric material 605 can be high-k dielectric material such as silicon nitride, aluminum oxide, hafnium oxide, or zirconium oxide. In one embodiment, the layer of high k-dielectric material 605 function to electrically isolate the two layers of conductive materials 604 and prevent leakage current from passing between the two layers of conductive materials 605. The thickness of 1, 2 or 3 nm for the dielectric layer 605 allows a high resolution to pinpoint a single molecule, such as the individual nucleotides in a ssDNA, as it passes through a nanopore 601 on the thin film. Since the funnel shaped nanopores cut through the multilayered thin film, each of the layers will form a circular through hole 606 at a section of the nanopore and this will make sure that any tilting of the molecule from the central axis of the nanopore will yield similar reading because the openings on the conductive layers are symmetric around the central axis. Since the sandwiched layer is detecting identity of the molecules, the section of the nanopore cutting through this structure has a diameter of 1, 2 or 3 nm to ensure accurate detection. The thin film may further comprise additional top and bottom layers of dielectric materials 607, 608 such as silicon oxide, or silicon nitride, for purposes such as providing structural support or electrical isolation from the surround environment. The additional layers would make up the portions of the thin film where the funnel-shaped nanopore is larger and facilitates the translocation of molecules into the final 1, 2 or 3 nm of the nanopore where detection occurs. The above mentioned range of 1-3 nm in the diameter of the nanopore and in the thickness of the high-k dielectric material is specifically chosen for nucleic acids. For other molecules, such as amino acids, proteins or peptides, a skilled person in the art will readily adjust the dimensions to optimize the detection signals.

Nanopore-Based Sequencing Biochip

Figure 7:
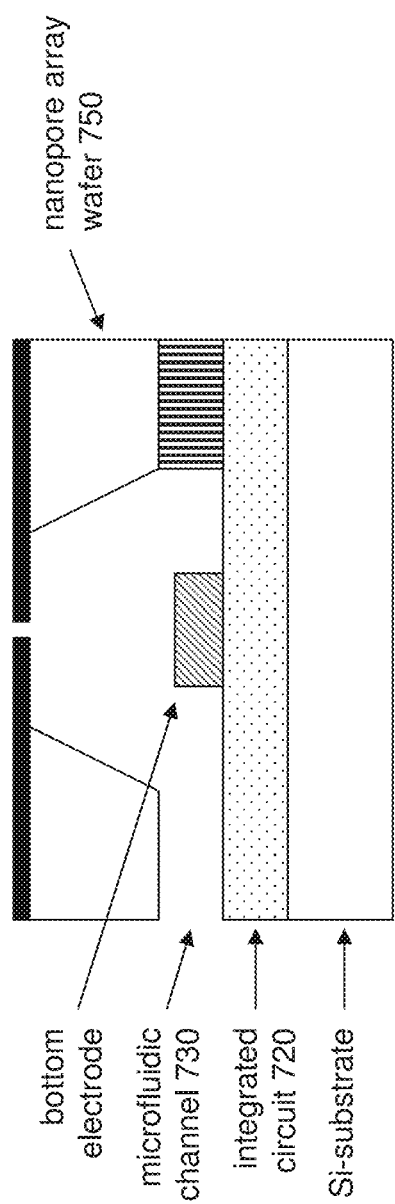
FIG. 7 illustrates one embodiment of a bonded nanopore array wafer and integrated circuit wafer to form the bottom cavity of a measurement chamber.

After the nanopore array is formed with either the subtractive or additive method, the nanopore array wafer 750 can be bonded onto a wafer with pre-fabricated integrated circuits 720 and microfluidics channels 730, as shown in FIG. 7. This completes the formation of the bottom cavity of the measurement chamber. The nucleic acid sample can be extracted out of the biochip through the microfluidic channels on the bottom wafer if desired.

Figure 8:
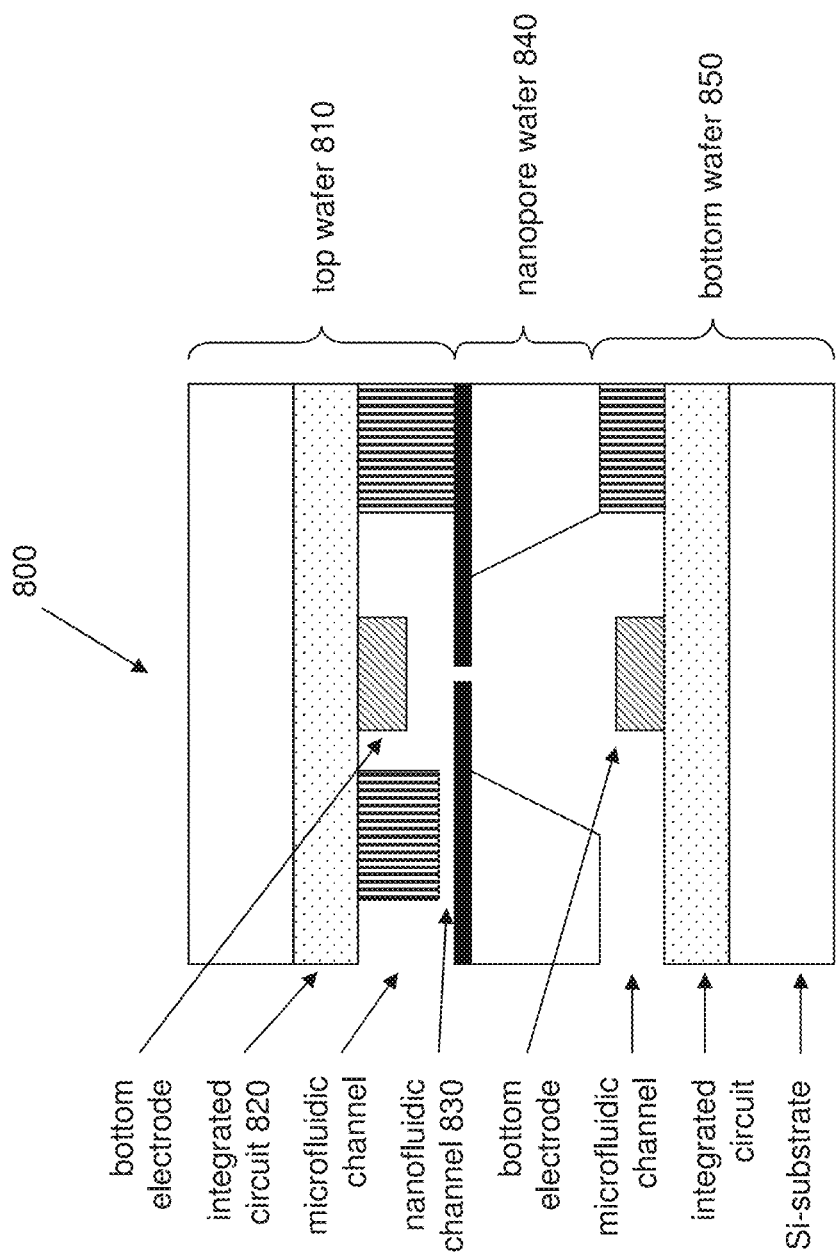
FIG. 8 illustrates one embodiment of a bonded top wafer and composite water to form the top cavity of the measurement chamber.
Figure 9:
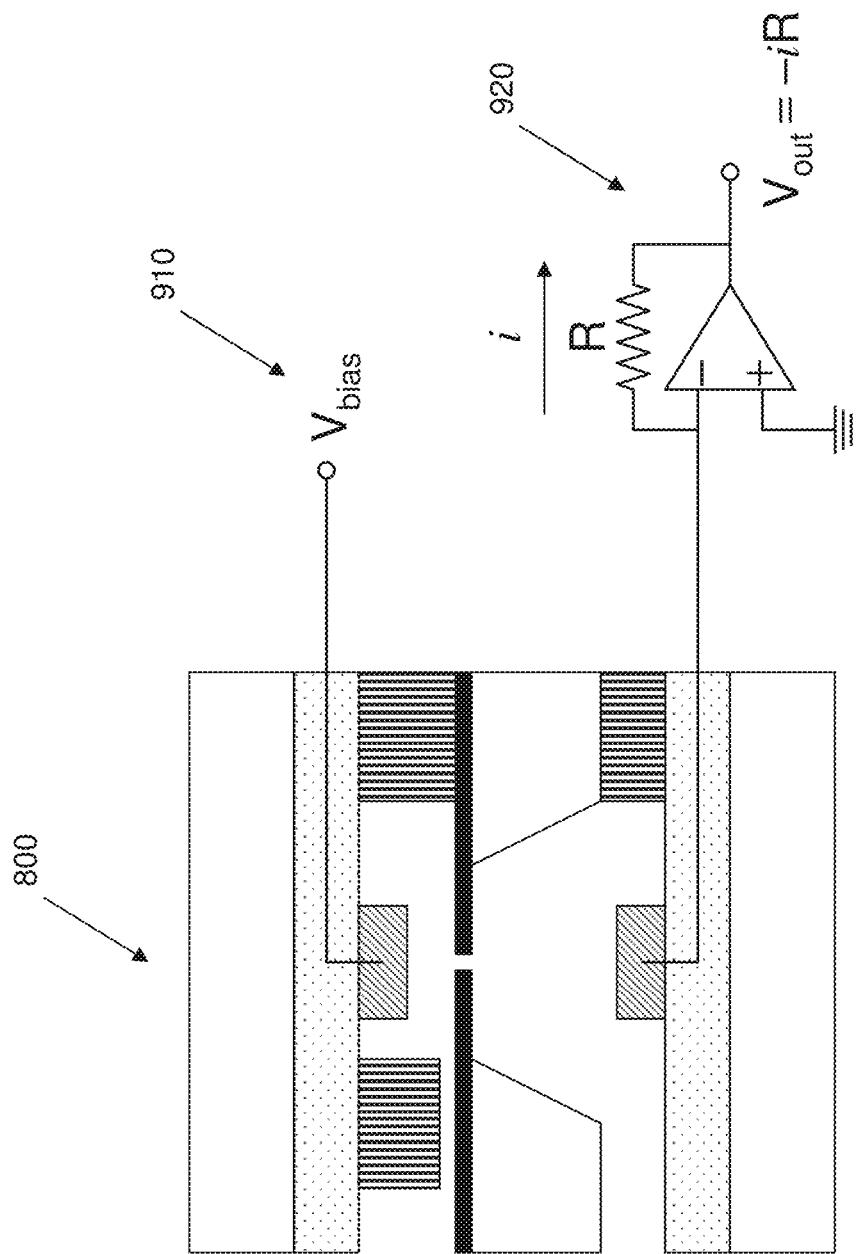
FIG. 9 illustrates one embodiment of a voltage biasing scheme and current sensing circuit operable with a nanopore-based sequencer.

Similarly, in some embodiments, the top cavity of the measurement chamber is formed by bonding a top wafer 810 with the integrated circuit 820 and/or the fluidic channels 830 onto the composite wafer, which includes the bonded nanopore wafer 840 and the bottom wafer 850. This trilayer wafer structure 800 is illustrated in FIG. 8. One embodiment of the voltage biasing scheme 910 and the associated current sensing circuit 920 are depicted in FIG. 9. With proper fluid. I/O connections, such as those with minimal dead-volume, the trilayer composite wafer 800 is then mounted on a supporting frame for wire bonding or bell grid wire bonding. Typical packaging techniques, for example, epoxy encapsulation and ceramic packaging, can be used to enclose the whole assemble to form the nanopore-based sequencing biochip. Alternatively, integrated circuits, such as those associated with sensing and biasing, may be fabricated on the nanopore wafer 840, which may be bonded to blank substrate instead of another wafer having integrated circuits thereon.

Figure 10A:
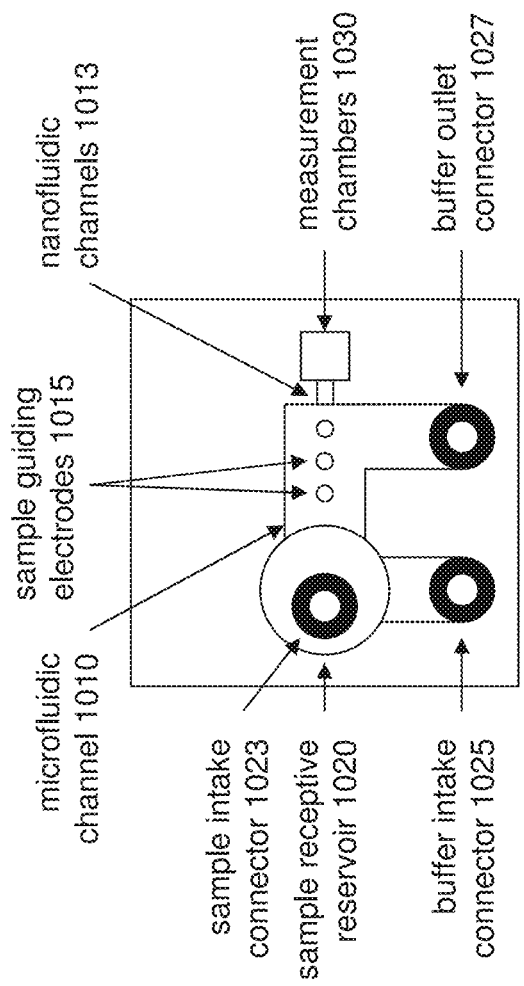
FIG. 10A illustrates one embodiment of a nanopore-based sequencer.
Figure 11:
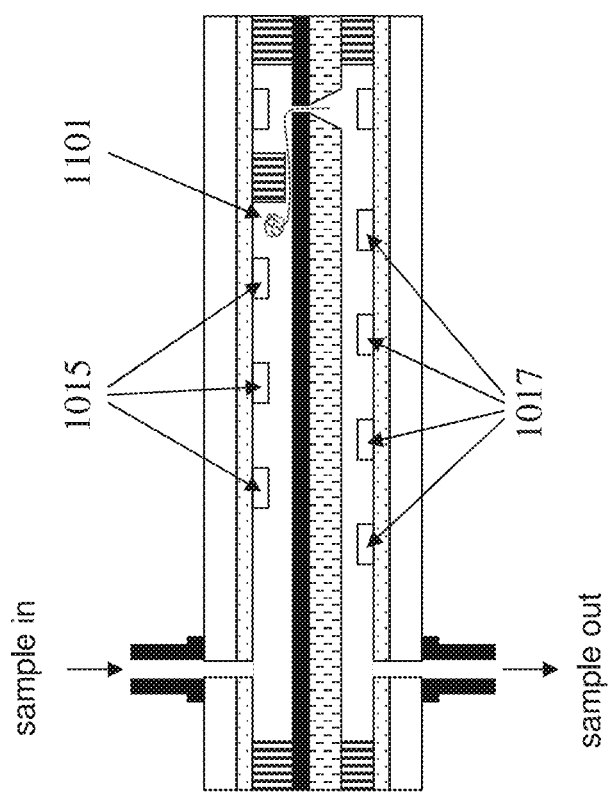
FIG. 11 illustrates a cross-sectional view of one embodiment of a nanopore-based sequencer along a selected path from the sample intake, along the microfluidic channel and the nanofluidic channel, through the measurement chamber, then to the sample outlet.

Furthermore, in some embodiments, there are two more features embedded on the top wafer 810, namely the sample guiding electrodes 1015 along the microfluidic channel 1010 and the nanofluidic channel 1013 leading to the measurement chamber 1030, as shown in FIGS. 10A and 11. To further illustrate the flow of sample through the nanopore-based sequencing biochip, one example is discussed in details below.

The buffer intake 1025 and buffer outlet 1027 are for pre-wet and pre-fill the network of microfluidic channel 1010, the nanofluidic channel 1013 and the measurement chamber 1030 before the intake of the sample for detection. During detection, the fluid flow in the microfluidic channel can be adjusted by the flow rate of the buffer intake and outlet using the on-chip or off-chip micropumps and microvalves.

In one example, the phosphate-deoxyribose backbone of a single strand nucleic acid molecule is charged with a negative charge for each base segment, and there are two negative charges at the 5'-end of the molecule. A positive voltage pulsating along the sample guiding electrode chain 1015 from the receptive reservoir 1020 through the sample intake connector 1023 to the destined measurement chamber 1030 can extract the nucleic acid molecule from the receptive reservoir 1020 and deliver the molecule to the pre-assigned measurement chamber 1030. Likewise, sample guiding electrodes 1017 also are embedded on the bottom wafer along the microfluidic channels 1010 for extracting the samples out of the nanopore-based sequencing biochip in a similar way.

Figure 10B:
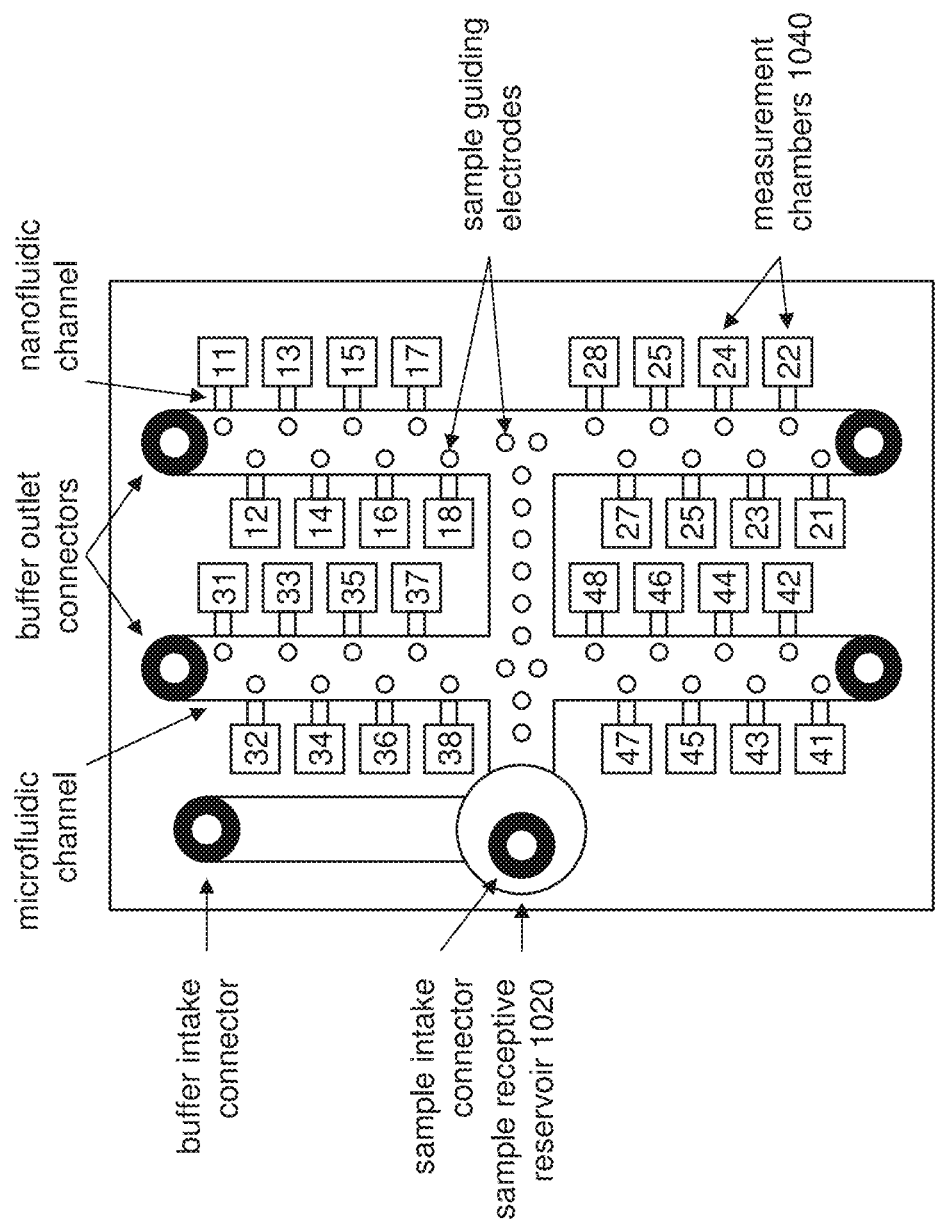
FIG. 10B illustrates one embodiment of multiple measurement chambers.

Using similar scheme of sample guiding electrodes along the network of fluidic channels, one can extend the number of measurement chambers 1040 to more than one. An example of the measurement chambers arranged in a tree architecture is illustrated in FIG. 10B. Besides the ability to perform multiple independent analyses, the order of the DNA fragments as they are being extracted from the sample receptive reservoir 1020 is pre-assigned to each measurement chamber in some embodiments. As shown in FIG. 10B, the measurement chambers 1040 are labeled with a 2-digit number. The first digit denotes the branch number and the second digit indicates the position of the measurement chamber in a branch. The assignment order of the measurement chambers 1040 may simply be in the ascending order, i.e., the chamber with the lowest number can be used first and then the chamber with next higher number. In this way, all of the measurement chambers in a branch can be used before moving onto the next branch. Alternatively, the samples can be assigned to the chambers with the lowest number in each branch with the lowest branch number being used first, i.e., 11, 21, 31, 41 then 12, 22, 32, 42, so on and so forth in the current example. According to this assignment approach, the measurement chamber of each branch with the furthest distance from the central microfluidic channel may be assigned first, then the next one of each branch. This approach may reduce the interference of the electrical signal of the sample guiding electrodes in the central microfluidic channel onto the measured signals. When the overall measurement is completed, the sequence of the entire DNA sample can be systematically assembled according to the order of extraction of the fragments. This may eliminate the time consuming post detection analysis required by other conventional sequencing technologies, such as, microarray, in which the hybridization process randomizes the original sequence of the sample and a computation intensive and error-prone post-detection analysis is required to piece back the proper sequence. Furthermore, since the order of extraction of the fragments is recorded, the fragments can be recombined to form the original DNA sample. For the other conventional sequencing technologies, the original sample is typically destroyed and cannot be retrieved for future use.

Referring back to FIG. 10A, the nanofluidic channel 1013 formed by wafer bonding of the top and composite wafer may serve as a filter, a sample flow rate controller, as well as a molecule stretcher. In some embodiments, the nanofluidic channel serves as a filter by turning on and off the top electrode on the top wafer, one can selectively pull in the sample from the microfluidic channel. In some embodiments, the nanofluidic channel serves as a sample flow rate controller by adjusting the voltages of the top and bottom electrodes, one can control the flow rate of the sample through the nanofluidic channel. The nanofluidic channel 1013 may also serve as a molecule stretcher because the single strand nucleic acid molecule 1101 may be stretched out from the natural curl up state when it passes through the nanofluidic channel 1013, as depicted in FIG. 11.

Figure 12:
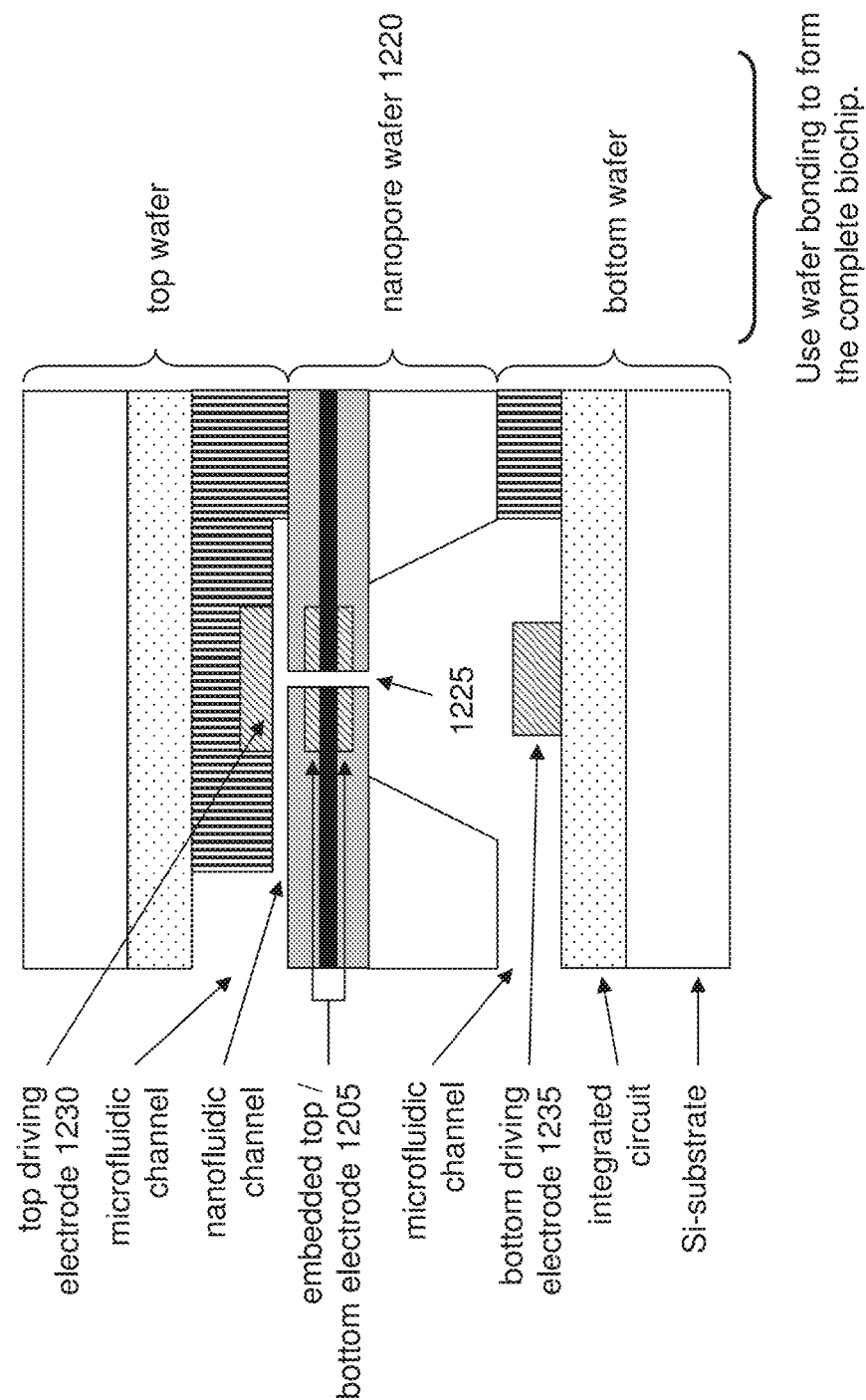
FIG. 12 illustrates one embodiment of a trilayer biochip structure with embedded electrodes.

In some embodiments, the speed control properties of the nanofluidic channels are exploited to allow more accurate analyses of molecules. As illustrated in FIG. 12, the sensing electrodes 1205 are embedded in the nanopore 1225, which become an integral part of the micro-/nano-channel network in controlling the flow of the molecules through the nanopore 1225. In addition to the nanofluidic channel, the applied DC voltages are designed to fine tune the speed and the direction of the molecules when translocating through the nanopore 1225. By alternating the magnitude of the DC biasing voltages is applied to the top and bottom driving electrodes 1230 and 1235, respectively, and the embedded sensing electrodes 1205, the molecule under test can be drawn through the nanopore 1225 back and forth multiple times for repeated analyses, in order to increase the accuracy in identifying the molecules by eliminating the statistical error, i.e., the false-positive error rate can be reduced.

Unlike some conventional approach, where the sensing electrodes are integrated into the nanopore, it might only take several nanoseconds for each base in the DNA to travel through the nanopore. Such transit time is too short for any meaningful measurement. In view of this shortcoming, other conventional approaches have been developed to slow down the movement of molecules through the nanopore. One conventional approach proposes a voltage trapping scheme to control the speed of the molecules by embedding extra electrodes into the nanopore. The proposed voltage trapping scheme is difficult to implement since it requires four or more conducting electrodes stacked on top of each other and electrically insulated from each other by sandwiching dielectric material in between the conducting electrodes. The required 2-3 nm nanopore forms on this multi-layer film may have an aspect ratio of more than 30:1, which is difficult, if not impossible, to achieve with the current integrated circuit fabrication technologies.

Figure 13A:
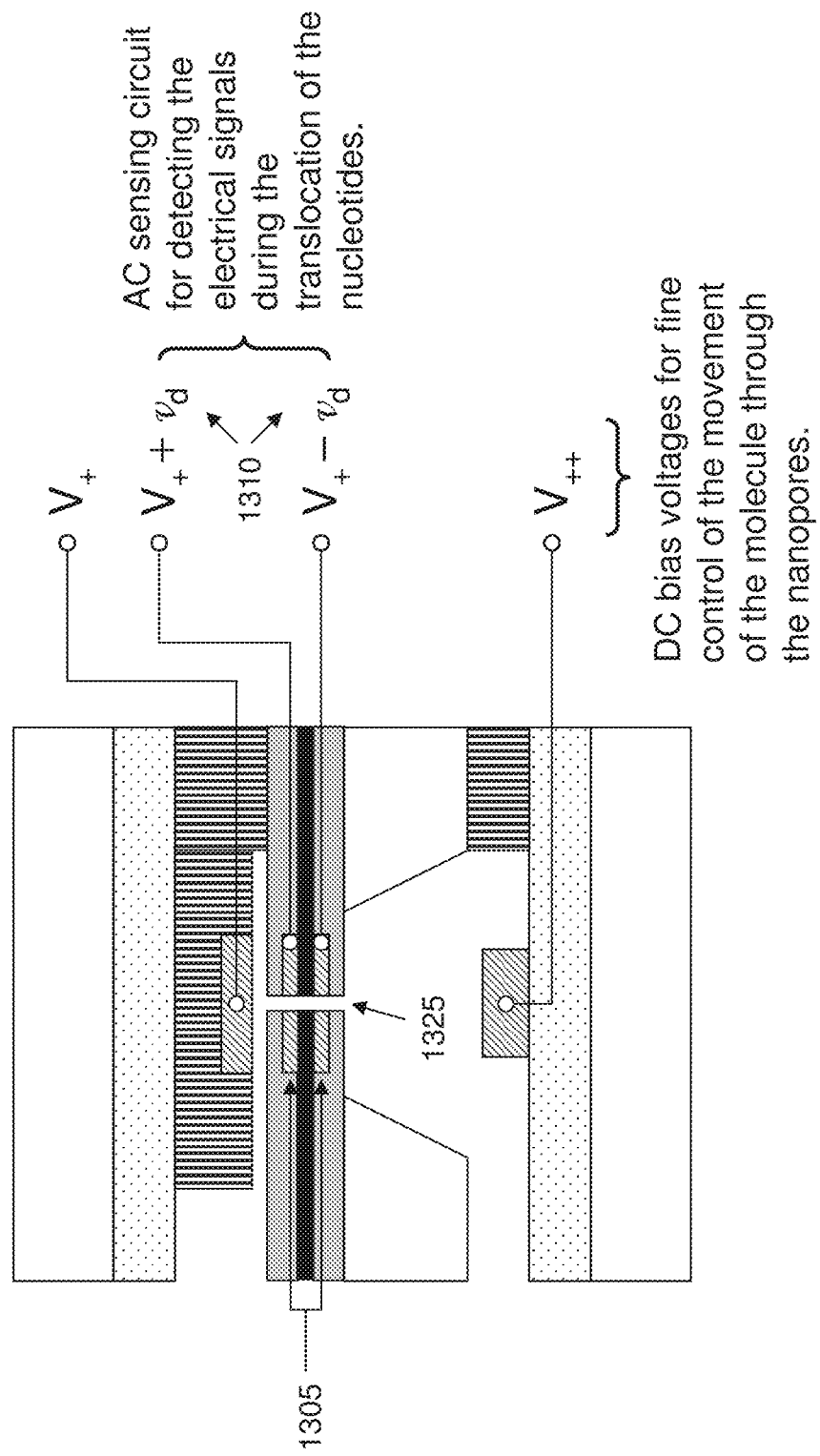
FIG. 13A illustrates one embodiment of a biasing and sensing scheme for nanopore detection.

As shown in FIG. 13A, the applied AC sensing voltages 1310 are for interrogating the molecules while they are translocating through the nanopore 1325. Consequently, various sensing mechanisms can be employed to identify the molecule, for instance, change in resistance, change in capacitance, change in phase and/or tunnelling current. Due to the close proximity of the embedded sensing electrodes 1305 and the molecules under test, signal-to-noise ratio can be improved.

Figure 13B:
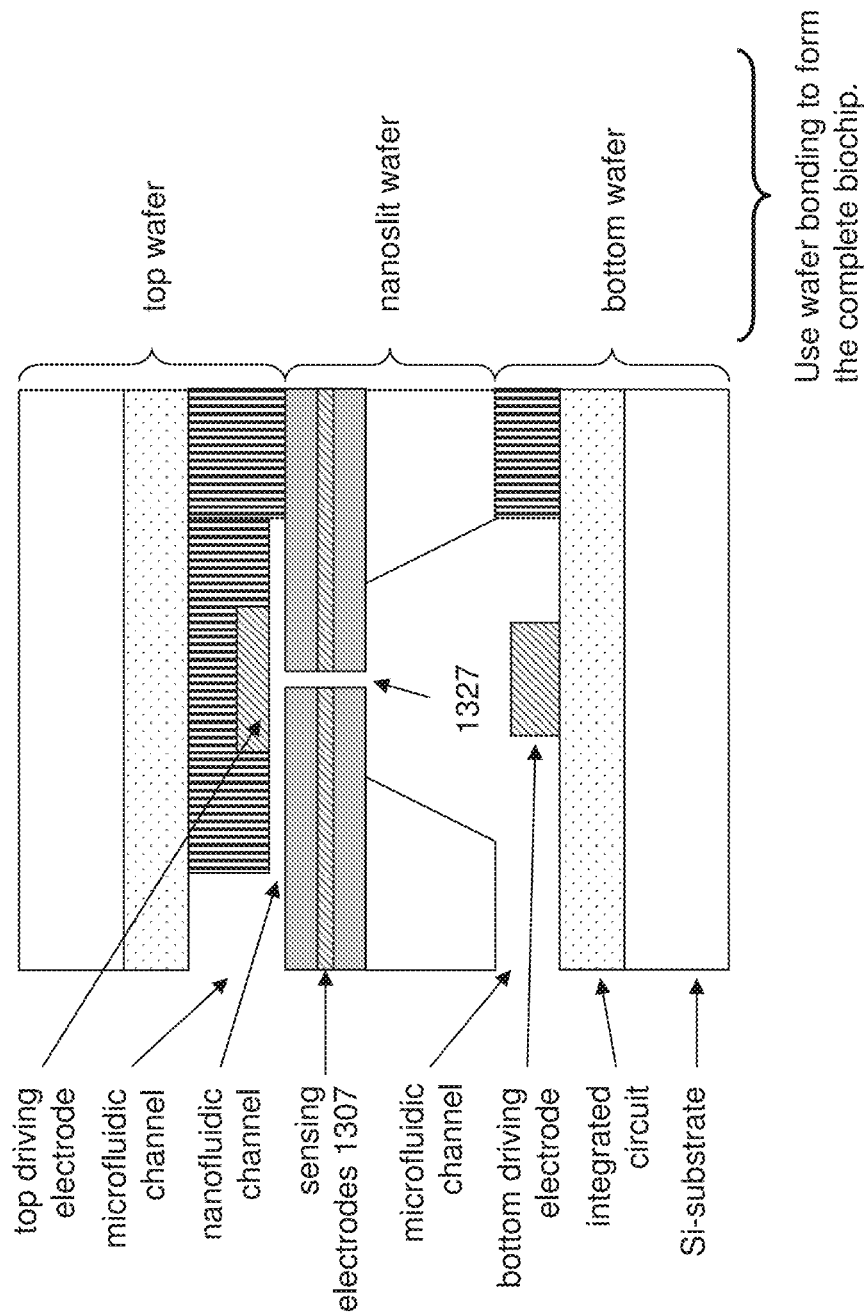
FIG. 13B illustrates one embodiment of a planar electrode implementation.

The above exemplary sample delivery and filtering mechanism serves as an example to illustrate how an array of nanopore measurement chambers can be implemented. One of skill in the art would recognize that variations to the above delivery and filtering mechanism may be adopted in different embodiments. Furthermore, array of pores with different sizes can be realized using the illustrated methods. Together with the protein pores, such as α-haemolysin, and the above mentioned array of solid-state nanopores, an array of bio-nanopores can also be realized. In some embodiments, both sensing electrodes may be placed onto the same conducting layer, instead of the stacked electrodes on different conducting layers described above. FIG. 13B illustrates one embodiment of this planar electrode implementation. In this planar electrode implementation, both sensing electrodes 1307 are placed on the same conducting layer, with a nanoslit 1327 defined in between the sensing electrodes 1307. A top view of the sensing electrodes 1307 and the nanoslit 1327 are illustrated in FIG. 13C. As discussed above, both nanopore and nanoslit can be defined using the nanopantography.

The ability to perform molecule detection substantially in real-time, the ability to perform single molecule detection without the pre-detection sample amplification, the ability to carry out multiple and substantially simultaneous detections, the ability to do multi-pass detection, the ability to identify the sample without the computation intensive post-detection analysis, and/or the ability to retain the sample after detection for future use are very crucial in providing a low cost, fast and accurate genomic analysis in some embodiments, for instance, in recognizing the single nucleotide polymorphism.

In this invention, the double strand DNA, dsDNA, is pretreated with nickases so that nicking actions occur at or near the designed restriction sites. The nicked dsDNA may be linearized before the individual oligonucleotides are dissociated from the nicked dsDNA in a dissociation zone according to their order on the dsDNA. Each oligonucleotide is then pulled into different arms of the guiding channels, e.g. H-tree structure channels, by the guiding electrodes. The sequence of each oligonucleotide will then be detected by the nanopore chip at downstream. When a set of H-tree structure channels is used, time for each oligonucleotide reaching the nanopore will roughly reflect the order of the oligonucleotide on the dsDNA because the path length from the singular inlet to the leaves in the balanced H-tree is designed to be identical. This order can be employed to assemble the detection results to obtain the sequence of the original dsDNA without a reference sequence. Since the two strands in dsDNA are complementary to each other, two oligonucleotides reaching the nanopore chip at about the same time are likely complementary to each other and the detected sequences of each pair of such oligonucleotides will counter check the correctness of each other, i.e. self-checking. When pairing up two maximally complementary oligonucleotides, the sequence of the overhangs at the two ends of each oligonucleotide caused by the intersperse nature of the restriction sites on the dsDNA will be used as matching criteria when searching for the neighboring pairs of oligonucleotides, i.e. self-guiding. Because of this built-in self-checking and self-guiding mechanism, the detected sequences of the oligonucleotides can be assembled together without a reference sequence, i.e. de novo sequencing can be achieved.

In one embodiment, a long dsDNA is fed into a chamber 1401 comprising enzymes for nicking at least one of the strands of DNA 1402 at specific restriction sites. In one embodiment, the dsDNA is straightened after being nicked by the enzyme. FIG. 14 shows embodiments for straightening the dsDNA. Enzyme for nicking the dsDNA includes mutated type II S endonucleoases such as fokI based nickase, and other newly discovered nickase or artificially engineered nickase included in New England BioLab's REBASE® database; CRISPR/cas9 derived nickases; TALEN like fokI based nickases. The enzymatically nicked DNA is then disrupted, e.g. by heat or enzyme, into short strands of ssDNA at a location downstream of where the enzymatic activity occurred or in a separate chamber. Since the nicked DNA will remain as a long double helix nonetheless with nicks after enzyme modification, the long nicked dsDNA can be controlled to feed towards a dissociation zone (e.g. by guiding electrodes) where short strands of ssDNA will dissociate from the long dsDNA one by one in a controlled manner. The dissociation can be achieved by heating or enzymes such as helicase. In one embodiment, the enzymes include the bacteriophage T7 gene product 4, or gp4, wild-type proteins or mutant derivatives. The short strands of ssDNA are then fed downstream via a single inlet that leads to multiple outlets. The total length of every path that leads from the inlet to an outlet is designed to be the same such that the arrival time of the ssDNA at the outlet would imply its order on the original dsDNA. Guiding electrodes will assign the ssDNA entering the inlet into different channels. In one embodiment, guiding electrodes will be along the entire channel to ensure the ssDNA arrives at the outlet. In one embodiment, the set of channels has a H-tree structure. FIG. 15 shows an example of the H-tree structure. At each of the outlet, the ssDNA would be translocated through a nanopore for reading of the sequence. Since the order of the ssDNA on the original long strand DNA is known, the entire sequence could be easily pieced back together after the individual ssDNA is read. An example of the concatenation algorithm for assembling the oligonucleotide sequences into the dsDNA sequence without a reference sequence is shown in FIG. 16.

Using a cluster of eight computer servers, each has dual Qual-core Xeon® processors (2.4 GHz) and 12 GB RAM, Lin and colleagues performed a comparison on seven de novo assembly algorithms, and noticed that the assembly time for these seven algorithms is ranging from several minutes to several hours for the *C. elegans* (20.9 Mbp, mega base pairs). [Ref: Lin, Yong, et al., "Comparative studies of de novo assembly tools for next-generation sequencing technologies," *Bioinformatics,* 2012 Aug. 1; 27(15): 2031-2037.]

In order to demonstrate the improvement in the aforementioned nickase sample preparation and the associated assembly algorithm, the nicking action and the assembly algorithm were implemented using Python in a MacBook Pro® laptop with a dual-core i5 processor (2.5 GHz) and 16 GB RAM. For a fair comparison with the other seven de novo assembly algorithms, the sequences of dsDNA with length of 20 Mbp were randomly generated, the nicks along the two strands of the dsDNA were generated according to the pattern of the pre-defined restriction site, and finally created the library (hash table) according to the sequences of the shortened ssDNA. Aligned with the other seven de novo assembly algorithms, simulations of several cases were conducted when the reading and the assembly of the ssDNA were sequentially performed, i.e. the assembly process would not start until all of results for the ssDNA were available. The typical assembly time using the method of this invention is less than five minutes, which means that a real time analysis on the sample DNA is feasible with a portable system. It is anticipated that the assembly time will be substantially shorten if the reading and the assembly of the ssDNA are concurrently being processed, as illustrated in the flow chart in FIG. 16.

In one embodiment, a DNA sample is amplified by a digital PCR, dPCR, before being processed for reading of the DNA sequence at the nanopore such that the sequence for a rare allele or for ultra-low abundance as in the case of liquid biopsy as well as cell-free DNA analyses. In another embodiment, the dPCR exists separately from the sequencing system. The dPCR of this invention comprises a set of channels having the H-tree structure as described above. In one embodiment, the set of channels is filled with hydrophobic fluid, has a higher boiling point than water, such as Fluorinert™, a synthetic oil from 3M™, or mineral oil. DNA sample is mixed with PCR assay reagents which is water based and then fed to the single inlet of the set of H-tree channels which dispenses a small volume of the DNA sample and reagents into a well at each of the multiple outlets. In one is embodiment, the wells are an array of pores fabricated on a silicon wafer. In another embodiment, the diameter of each well range from 10 to 1000 µm. The control of temperature required for PCR is achieved by embedding sensors and heating elements in the silicon wafer having the array of wells or by placing the entire water in an environment with controlled temperature. In one embodiment, fluorescent signals from each of the wells are recorded by CMOS or CCD coupled to each well. For dPCR within a sequencing system, the samples from one or more selected wells will be allowed to proceed downstream for processes required for reading of the DNA sequence at the funnel-shaped nanopore. When the dPCR exists as a separate device, the array of pores, which are connected to the outlet of the H-tree structure channels at one of the openings, is sealed by a membrane which can be removed if the DNA sample is to be retrieved. An embodiment of a separate dPCR in this invention is shown in FIGS. 17 and 18. In this embodiment, the dPCR consists of a well array and a H-tree microfluidic network, Each outlet of the H-tree microfluidic network is connected to a corresponding well on the well array when fabricated. The side of the well array 1701, which is not connected to the microfluidic network, is covered by a transparent film to form the top channel while the side of the H-tree microfluidic network 1702 that is not connected to the well array is covered with a supporting slab. Both of the transparent film and the supporting slab have been omitted from FIG. 17 for the sake of clarity. The I/O ports have also been omitted from FIG. 17. The complete real-time dPCR module is displayed in FIG. 18. The input ports for oil and sample, and the excess receptacle are included but the transparent film has been omitted. In one embodiment, sample loading of the dPCR is as follows: 1) partially filling the module with synthetic oil, 2) loading the sample liquid into the channel, and 3) pumping in further synthetic oil to push the sample liquid into the wells. The sample liquid is expected to be evenly distributed into each well if the fluidic channels are properly designed and manufactured e.g. H-tree microfluidic network. After loading, the sample liquid is trapped by the oil in the front and in the back. No water will be lost due to evaporation, i.e. the concentration of the essay is maintained throughout the sample loading process. Since the input sample liquid has limited volume and is expected to be less than the total volume of all the wells in the array, the initial body of the sample liquid will break up into smaller, but equal, volumes at each successive level in the hierarchical fluidic network. Eventually, the final 'droplets' will be partitioned into different wells. The location of each droplet is fixed in the array before, during and after the temperature cycle. The florescent images for different wavelengths of each cycle in the temperature cycle can be captured with an external imaging device. This means that the progress of PCR can be monitored in real-time, i.e. real-time dPCR. When there is a need, one can use a needle to punch through the transparent film and use a syringe or a hollow optical fiber to extract the interested droplet from the well for further processes. The dPCR chip can be fabricated by one or more of the following techniques based the well size. In one embodiment, 3D-printing or molding is used for fabricating wells having diameters of several hundreds of microns. In another embodiment, nano-3D printing or micro-molding is used for fabricating wells having diameters of hundred to tens of microns. In a further embodiment, nanoimprint on thermal plastic or semiconductor fabrication techniques on silicon is used for fabricating wells having diameters of tens to several microns. For the case of silicon chips, we can integrate the heating element onto the chip for rapid thermal cycling.

A skilled person in the art will readily recognize that the H-tree architecture can also be used in other applications. In one embodiment, instead of DNA molecules, other biological substances, such as individual cells, can be captured into different wells for performing multiple single cell experiments.

Nanopore-Based Sequencer

Nanopore-based sequencer provides a portable genomic detection and analysis system. In some embodiments, the nanopore-based sequencer includes two major components, namely hardware and software. Some embodiments of the high level architectures and subunits are discussed below.

A. Hardware System

In some embodiments, the hardware system of nanopore-based sequencer includes two major units, namely the computing, communication and control unit and the nanopore-based sequencing biochip interface unit, and various modules. One embodiment of the high level architecture is shown in FIG. 19. The details of various parts are further explained below.

I. Computing, Communication, and Control Unit

In one embodiment, the hardware system 1900 includes a portable computing system with a display device 1910. This may be implemented using a tablet, a laptop, a netbook, an all-in-one desktop computer, a smartphone, a personal digital assistant (PDA) or any handheld computing devices, etc. It serves as the central unit for running the operating system (OS), executing the data analysis software, storing data, controlling the operation of the nanopore-based sequencing biochip, and collecting data from the nanopore-based sequencing biochip.

In one embodiment, the hardware system 1900 further includes a network communication module 1920.

The network communication module 1920 includes one or more of WiFi, WiMAX, Ethernet, Bluetooth®, telephone capability, satellite link, and Global Positioning System (GPS), etc. The network communication module 1920 serves as the communication hub for communicating with the central computing system for data sharing, program update, data analysis, etc., communicating with other computing devices such that the data can be shared and the data analysis can be run in parallel in multiple computing devices, communicating with other Bluetooth® enabled devices (e.g., cellular telephone, printer, etc.), data sharing, program update, etc., and sending and receiving the GPS signal.

In one embodiment, the hardware system 1900 further includes an input device 1930. The input device 1930 may include one or more of a keyboard, a touch screen, a mouse, a trackball, infrared (IR) pointing device, and voice recognition device, etc. The input device 1930 serves as the human interface for command entry and data entry.

In one embodiment, the hardware system 1900 further includes an input/output (I/O) port 1940, which may include a flash memory card interface, an IEEE 1394 interface, and a Universal Serial Bus (USB) interface, etc. The I/O port 1940 serves as a serial interface with other electronic devices, a secondary data storage interface, and measurement data I/O for the nanopore-based sequencing biochip.

II. Nanopore-Based Sequencing Biochip Interface Unit

In some embodiments, a nanopore-based sequencing (nSeq) biochip interface unit 1950 couples to an nSeq electronic module 1960, a fluid control module 1970, a chemical storage and fluid I/O connection module 1980, and an nSeq fluid control and sample I/O connection module 1990. The nSeq electronic module 1960 controls the distribution of nucleic acid module, control the flow rate of the nanofluidic channels, collect measurement data, and output data to the computing, communication, and control unit.

In some embodiments, the fluid control module 1970 controls the fluid flow between the chemical storage and the nSeq biochip via the buffer intake/outlet connectors and the use of the on-chip or off-chip micropumps and microvalves. The chemical storage and fluid I/O connection module 1480 can supply chemical to the nSeq biochip, if needed, and can also serve as a chemical and/or bio-waste storage. The nSeq fluid control and sample I/O connection module 1990 can control the fluid and sample flow in the nSeq biochip as well as control the sample intake and outlet of the nSeq biochip. For instance, referring back to FIG. 10B, if one wants to perform detection at measurement chamber #11, the buffer outlet for branch #1 will be opened while all of the other buffer outlets are closed. As a result, the fluid will flow from the sample intake toward branch #1 and works in synchronous with the sample guiding electrodes along the microfluidic channels to deliver the sample to measurement chamber #11.

B. Software Architecture

FIG. 20 illustrates a high-level architecture of the software and related hardware components for the operating system and the genomic analysis software in one embodiment of a nanopore-based sequencer. Various logic processing modules in the software architecture shown can be implemented by processing devices (such as the portable computing system 1910 in FIG. 19) executing instructions embodied in computer-readable medium. A computer-readable medium includes any mechanism that provides (i.e., stores and/or transmits) information in a form accessible by a computer (e.g., a server, a personal computer, network device, personal digital assistant, manufacturing tool, any device with a set of one or more processors, etc.). For example, a computer-readable medium includes recordable/non-recordable media (e.g., read only memory (ROM); random access memory (RAM); magnetic disk storage media; optical storage media; flash memory devices; etc.); etc.

As mentioned above, an operating system 2010 is installed in the computing, communication and control unit. The operating system 2010 may include Windows, Linux, or any operating system suitable for computing devices. Aside from the operating system 2010 installed in the computing, communication and control unit, the genomic analysis software further includes five processing modules, namely, a graphical user interface (GUI) 2020, a data viewer 2030, a genomic data analyzer interface 2040, a genomic data analyzer 2050, and a genomic database 2060. Some embodiments of the interaction between the operating system 2010, the above processing modules 2020-2060, and the other hardware components are discussed below with reference to FIG. 20.

In some embodiments, the genomic data analyzer interface 2040 acts as a data flow control unit in the genomic analysis software architecture. After obtaining the commands and/or input data from the input device, the operating system 2010 transmits the information to the genomic data analyzer 2050 through the genomic data analyzer interface 2040. The genomic data analyzer 2050 then acts accordingly. With the proper commands (e.g., GET, ADD, etc.), the genomic data analyzer interface 2040 controls the data flow between the I/O port 2070 and the genomic database 2060, so the data stored in the database 2060 can be sent out or updated. Similarly, the analyzer software can be periodically updated via the I/O port 2070 and/or the input devices 2080. The genomic data analyzer interface 2040 is also coupled to the nSeq biochip interface 2090 to monitor the nSeq biochip. The status of the nSeq biochip is monitored and shown in a display unit (such as the display device in the portable computing system 1910 in FIG. 19) via the analyzer interface 2040. The genomic data analyzer interface 2040 also takes the results from the genomic data analyzer 2050 and shows them in the display unit.

In some embodiments, the genomic data analyzer 2050 is the main data analysis unit of the genomic analysis software. It obtains the measurements from the nSeq biochip, performs analysis and then compares the results with the data stored in the database 2060 to identify the bio-agents. The analysis results can be shown in the display unit and stored in the database 2060 for future reference.

The genomic database 2060 is a data repository for storing the existing bio-agents and newly discovered nucleic acid sequences. The data viewer 2030 includes software routines that take the data and information from some or all of the other units and show them on the display device.

Thus, a method and apparatus for portable real-time analysis and identification is of molecules has been described. It will be apparent from the foregoing description that aspects of the present invention may be embodied, at least in part, in software. That is, the techniques may be carried out in a computer system or other data processing system in response to its processor executing sequences of instructions contained in a memory. In various embodiments, hardwired circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller.

In one embodiment, this invention provides a device for maintaining order of short strands of single stranded DNA dissociated from a nicked double strand DNA, comprising: a dissociation zone for dissociating said nicked double stranded DNA into short strands of single stranded DNA; a set of channels comprising a single inlet and a plurality of outlets, wherein length of each channel from said inlet to any one of said plurality of outlet is same and said inlet is downstream of said dissociation zone; and a set of guiding electrodes within said set of channels, wherein said guiding electrodes assigns each oligonucleotide into a separate channel in said set of channels.

In one embodiment, said dissociation zone comprises a mechanism for straightening said nicked double stranded DNA. In another embodiment, said mechanism comprises an array of micro- or nano-pillars. In a further embodiment, said mechanism comprises a DNA pump.

In one embodiment, said dissociation zone comprises a heating source.

In one embodiment, said dissociation zone comprises helicase.

In one embodiment, said set of channels has an H-tree structure.

In one embodiment, said device further comprises a well at each of said outlets.

In one embodiment, this invention provides a device for digital PCR, comprising: a dissociation zone for dissociating a nicked double stranded DNA into short strands of single stranded DNA; a set of channels comprising a single inlet and a plurality of outlets, wherein length of each channel from said inlet to any one of said plurality of outlet is same and said inlet is downstream of said dissociation zone; a set of guiding electrodes within said set of channels, wherein said guiding electrodes assigns each oligonucleotide into a separate channel in said set of channels; and a well array comprising two sides, wherein one of said two sides comprises wells which are each connected to an outlet of said set of channels and one of said two sides comprises a transparent film.

In one embodiment, said dissociation zone comprises a mechanism for straightening said nicked double stranded DNA. In one embodiment, said mechanism comprises an array of micro- or nano-pillars. In one embodiment, said mechanism comprises a DNA pump.

In one embodiment, said dissociation zone comprises a heating source.

In one embodiment, said dissociation zone comprises helicase.

In one embodiment, said set of channels has an H-tree structure.

In one embodiment, this invention provides a method for loading the device of this invention, comprising partially filling the set of channels with synthetic oil; loading a sample liquid into the inlet of said set of channels; and pumping in further synthetic oil to push said sample liquid into the wells.

In one embodiment, this invention provides a nano-pore sequencer, comprising: a dissociation zone for dissociating said nicked double stranded DNA into short strands of single stranded DNA; a set of channels comprising a single inlet and a plurality of outlets, wherein length of each channel from said inlet to any one of said plurality of outlets is same and said inlet is downstream of said dissociation zone; a set of guiding electrodes within said set of channels, wherein said guiding electrodes assigns each oligonucleotide into a separate channel in said set of channels; and a nanopore array wafer comprising a plurality of nanopores, wherein each of said plurality of nanopores is connected to one of said plurality of outlets.

In one embodiment, said dissociation zone comprises a mechanism for straightening said nicked double stranded DNA.

In one embodiment, said dissociation zone comprises a heating source or helicase.

In one embodiment, said set of channels has an H-tree structure.

In one embodiment, this invention provides a method of nanoslit-based sequencing, comprising: receiving measurement data from a nanoslit-based sequencing chip in a portable molecular analyzer, wherein the measurement data is related to a sample of molecules input to the portable molecular analyzer; and analyzing performing analysis of the measurement data to identify molecules in the sample, nanoslit-based sequencing chip is configured to measure one or more electrical characteristics of said sample of molecules and comprises a nanoslit array wafer defining a plurality of nanoslits each comprising at least one pair of embedded sensing electrodes, wherein each pair of said embedded sensing electrodes are located on opposite sides of said nanoslit.

In one embodiment, said nanoslit-based sequencing chip obtains the measurement data by detecting a change in resistance, change in capacitance, change in phase, or change in current in at least one of the plurality of nanoslits using said at least one pair of embedded sensing electrodes. In one embodiment, said current comprises a tunneling current.

In one embodiment, each of the plurality of nanoslits are in fluid communication with one or more nanofluidic channels and one or more microfluidic channels.

In one embodiment, said nanoslit-based sequencing chip obtains the measurement data by performing voltage trapping using said at least one pair of embedded sensing electrodes to control the speed of translocation of the molecule through the nanoslit.

In one embodiment, said nanoslit-based sequencing chip obtains the measurement data by applying an alternating current using said at least one pair of embedded sensing electrodes to detect electrical signals during translocation of the molecule through the nanoslit.

In one embodiment, said nanoslit-based sequencing chip obtains the measurement data by applying a voltage potential to at least one of the plurality of nanoslit using electrodes external to the plurality of nanoslits.

In one embodiment, this invention provides a portable molecule analyzer for performing the sequencing method of claim 1, comprising: a sample intake configured to receive a sample; and a nanoslit-based sequencing chip configured to measure one or more electrical characteristics of the sample; wherein said nanoslit-based sequencing chip is in fluid communication with said sample intake, said nanoslit-based sequencing chip comprises a nanoslit array wafer defining a plurality of nanoslits each comprising at least one pair of embedded sensing electrodes, wherein each pair of said embedded sensing electrodes are located on opposite sides of said nanoslit.

In one embodiment, each of said plurality of nanoslits comprises a plurality of layers made of different materials.

In one embodiment, each pair of said embedded sensing electrodes has a first electrode and a second electrode, said first and second electrodes are at the same depth along the length of said nanoslit.

In one embodiment, the plurality of embedded sensing electrodes are formed within at least two layers of the at least one nanoslit.

In one embodiment, the plurality of embedded sensing electrodes are configured to detect a change in resistance, change in capacitance, change in phase, or change in current in the at least one nanoslit.

In one embodiment, said current comprises tunneling current.

In one embodiment, said portable molecule analyzer further comprises a top electrode affixed to the portable molecule analyzer above at least one of the plurality of nanoslits, and a bottom electrode affixed to the portable molecule analyzer below said at least one nanoslit, wherein said at least one nanoslit provides a path for electrical communication between the top electrode and the bottom electrode.

In one embodiment, the bottom electrode or the top electrode is in electrical communication with an integrated circuit.

In one embodiment, the integrated circuit comprises a voltage biasing scheme or a current sensing circuit.

In one embodiment, said nanoslit-based sequencing chip comprises a nanoslit array wafer defining a plurality of nanoslits each in fluid communication with one or more nanofluidic channels and one or more microfluidic channels.

In one embodiment, said one or more microfluidic channels comprise guiding electrodes configured to guide a sample along the one or more microfluidic channels, or wherein said one or more nanofluidic channels comprise guiding electrodes configured to guide a sample along the one or more nanofluidic channels.

In one embodiment, this invention provides a portable molecule analyzer for performing a sequencing method, comprising: a sample intake configured to receive a sample; and a nanopore-based sequencing chip configured to measure one or more electrical characteristics of the sample; wherein said nanopore-based sequencing chip is in fluid communication with said sample intake, said nanopore-based sequencing chip comprises a nanopore array wafer defining a plurality of nanopores each comprising at least one pair of embedded sensing electrodes, wherein each pair of said embedded sensing electrodes are located on opposite sides of said nanopores.

In one embodiment, said nanopore-based sequencing chip is: a nanopore-based sequencing chip, comprising: a first set of one or more sample guiding electrodes, which guide a sample toward a measurement chamber; a second set of one or more sample guiding electrodes, which guide the sample away from the measurement chamber; a nanopore array wafer comprising a plurality of nanopores; a top wafer bonded to a top side of the nanopore array wafer; a bottom wafer bonded to a bottom side of the nanopore array wafer; one or more nanofluidic channels defined by the top wafer and the nanopore array wafer; one or more microfluidic channels defined by the bottom wafer and the nanopore array wafer; and a plurality of measurement chambers, wherein each of the plurality of measurement chambers comprises a nanopore, a top driving electrode and a bottom driving electrode; or a nanopore-based sequencing chip, comprising: a nanopore array wafer, said nanopore array wafer comprising two layers of conductive materials sandwiching a layer of dielectric material and a plurality of nanopores that cuts across the thickness of the nanopore array wafer; a top wafer bonded to a top side of the nanopore array wafer; a bottom wafer bonded to a bottom side of the nanopore array wafer, one or more nanofluidic channels defined by the top wafer and the nanopore array wafer; and one or more microfluidic channels defined by the bottom wafer and the nanopore array wafer; wherein an AC sensing current is applied across said two layers of conductive materials to interrogate molecules translocating through said plurality of nanopores.

It should be appreciated that references throughout this specification to "one embodiment" or "an embodiment" means that a particular feature, structure or characteristic described in connection with the embodiment is included in at least one embodiment of the present invention. Therefore, it is emphasized and should be appreciated that two or more references to "some embodiments" or "one embodiment" or "an alternative embodiment" in various portions of this specification are not necessarily all referring to the same embodiment. Furthermore, the particular features, structures or characteristics may be combined as suitable in one or more embodiments of the invention. In addition, while the invention has been described in terms of several embodiments, those skilled in the art will recognize that the invention is not limited to the embodiments described. The embodiments of the invention can be practiced with modification and alteration within the scope of the appended claims. The specification and the drawings are thus to be regarded as illustrative instead of limiting on the invention.

What is claimed is:

1. A portable molecule analyzer, comprising:
   (a) a sample intake configured to receive a sample; and
   (b) a funnel-shaped nanopore-based sequencing chip configured to measure one or more electrical characteristics of the sample;
   wherein said funnel-shaped nanopore-based sequencing chip is in fluid communication with said sample intake, said funnel-shaped nanopore-based sequencing chip comprises a funnel-shaped nanopore array wafer defining a plurality of funnel-shaped nanopores, each of said funnel-shaped nanopores comprises one pair of embedded sensing electrodes, which are located on two separate layers along the depth of each of said funnel-shaped nanopores and comprises a hole that fits exactly to the interior of each of said funnel-shaped nanopores; wherein said funnel-shaped nanopore array wafer is fabricated by ion milling through a film on a wafer using nanopantography; said film comprises two conductive layers sandwiching a dielectric layer of 1 to 3 nm in thickness; each of said funnel-shaped nanopores comprises a first opening at the wafer and a second opening at the film, wherein said first opening is larger than said second opening; said second opening has a diameter of 1 to 3 nm; wherein said two conductive layers form said pair of embedded sensing electrodes.

2. The portable molecule analyzer of claim 1, wherein each of said plurality of funnel-shaped nanopores comprises a plurality of layers made of different materials.

3. The portable molecule analyzer of claim 1, wherein said embedded sensing electrodes have a first electrode and a second electrode, said first and second electrodes are at the same depth along the length of each of said funnel-shaped nanopores.

4. The portable molecule analyzer of claim 1, wherein a plurality of embedded sensing electrodes are formed within at least two layers of each of said funnel-shaped nanopores.

5. The portable molecule analyzer of claim 1, wherein a plurality of embedded sensing electrodes are configured to detect a change in resistance, change in capacitance, change in phase, or change in current in each of said funnel-shaped nanopores.

6. The portable molecule analyzer of claim 5, wherein said current comprises tunneling current.

7. The portable molecule analyzer of claim 1, wherein said portable molecule analyzer further comprises a top electrode affixed to the portable molecule analyzer above each of said funnel-shaped nanopores, and a bottom electrode affixed to the portable molecule analyzer below each of said funnel-shaped nanopores, wherein each of said funnel-shaped nanopores provides a path for electrical communication between the top electrode and the bottom electrode.

8. The portable molecule analyzer of claim 7, wherein the bottom electrode or the top electrode is in electrical communication with an integrated circuit.

9. The portable molecule analyzer of claim 8, wherein the integrated circuit comprises a voltage biasing scheme or a current sensing circuit.

10. The portable molecule analyzer of claim 1, wherein each nanopore is in fluid communication with one or more nanofluidic channels and one or more microfluidic channels.

11. The portable molecule analyzer of claim 10, wherein said one or more microfluidic channels comprise guiding electrodes configured to guide a sample along the one or more microfluidic channels, or wherein said one or more nanofluidic channels comprise guiding electrodes configured to guide a sample along the one or more nanofluidic channels.

12. A method of funnel-shaped nanopore-based sequencing using the portable molecule analyzer of claim 1, comprising:
    (a) receiving measurement data from said funnel-shaped nanopore-based sequencing chip in said portable molecular analyzer, wherein the measurement data is related to one or more electrical characteristics of a sample of molecules input to the portable molecular analyzer; and
    (b) performing analysis of the measurement data to identify molecules in the sample.

13. The method of claim 12, wherein said funnel-shaped nanopore-based sequencing chip obtains the measurement data by detecting a change in resistance, change in capacitance, change in phase, or change in current in at least one of the funnel-shaped nanopores from said plurality of funnel-shaped nanopores using at least one pair of embedded sensing electrodes in at least one of the funnel-shaped nanopores.

14. The method of claim 13, wherein said current comprises a tunneling current.

15. The method of claim 12, wherein each of the funnel-shaped nanopores are in fluid communication with one or more nanofluidic channels and one or more microfluidic channels.

16. The method of claim 12, wherein said funnel-shaped nanopore-based sequencing chip obtains the measurement data from at least one of the funnel-shaped nanopores from said plurality of funnel-shaped nanopores by performing voltage trapping using at least one pair of embedded sensing electrodes in said at least one of the funnel-shaped nanopores to control the speed of translocation of a molecule through at least one of the funnel-shaped nanopores.

17. The method of claim 12, wherein said funnel-shaped nanopore-based sequencing chip obtains the measurement data during translocation of a molecule through at least one of the funnel-shaped nanopores from said plurality of funnel-shaped nanopores by applying an alternating current using at least one pair of embedded sensing electrodes in at least one of the funnel-shaped nanopores.

18. The method of claim 12, wherein said funnel-shaped nanopore-based sequencing chip obtains the measurement data by applying a voltage potential to at least one of the funnel-shaped nanopores from said plurality of funnel-shaped nanopores using one or more electrodes external to the funnel-shaped nanopores.

19. The method of claim 12, wherein said electrical characteristics comprises one or more of turn-on voltage, conductance and current across a molecule in the sample of molecules.

* * * * *

UNITED STATES PATENT AND TRADEMARK OFFICE
CERTIFICATE OF CORRECTION

| | | |
|---|---|---|
| PATENT NO. | : 11,565,258 B2 | Page 1 of 1 |
| APPLICATION NO. | : 16/338996 | |
| DATED | : January 31, 2023 | |
| INVENTOR(S) | : So et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 806 days.

Signed and Sealed this
Fourteenth Day of January, 2025

Derrick Brent
*Acting Director of the United States Patent and Trademark Office*